(12) United States Patent
Olson et al.

(10) Patent No.: US 7,641,091 B2
(45) Date of Patent: Jan. 5, 2010

(54) STAPLE DRIVE ASSEMBLY

(75) Inventors: Lee Ann Olson, Wallingford, CT (US); Ralph Stearns, Bozrah, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 92 days.

(21) Appl. No.: 11/242,761

(22) Filed: Oct. 4, 2005

(65) Prior Publication Data

US 2007/0075115 A1    Apr. 5, 2007

(51) Int. Cl.
*A61B 17/00* (2006.01)

(52) U.S. Cl. .................. 227/175.1; 227/19; 227/178.1; 227/179.1

(58) Field of Classification Search .................. 227/19, 227/178.1, 179.1, 181.1, 175.1
See application file for complete search history.

(56) References Cited

U.S. PATENT DOCUMENTS

| | | | |
|---|---|---|---|
| 3,079,606 A | | 3/1963 | Bobrov et al. |
| 3,317,105 A | | 5/1967 | Astafjev et al. |
| 3,490,675 A | | 1/1970 | Green et al. |
| 3,499,591 A | | 3/1970 | Green |
| 4,054,108 A | * | 10/1977 | Gill ............................ 123/54.4 |
| 4,106,446 A | * | 8/1978 | Yamada et al. ............ 123/90.13 |
| 4,111,206 A | | 9/1978 | Vishnevsky et al. |
| 4,244,372 A | | 1/1981 | Kapitanov et al. |
| 4,312,685 A | * | 1/1982 | Riedl ......................... 148/500 |
| 4,580,712 A | * | 4/1986 | Green ........................ 227/19 |
| 4,605,001 A | | 8/1986 | Rothfuss et al. |
| 4,610,383 A | | 9/1986 | Rothfuss et al. |
| 4,619,391 A | * | 10/1986 | Sharkany et al. ............... 227/19 |
| 4,633,874 A | | 1/1987 | Chow et al. |
| 4,662,555 A | * | 5/1987 | Thornton ..................... 227/19 |
| 4,669,647 A | * | 6/1987 | Storace ....................... 227/19 |
| 4,955,959 A | * | 9/1990 | Tompkins et al. ........ 227/178.1 |
| 4,978,049 A | | 12/1990 | Green |
| 5,014,899 A | | 5/1991 | Presty et al. |

(Continued)

FOREIGN PATENT DOCUMENTS

EP      0 669 104      8/1995

(Continued)

OTHER PUBLICATIONS

European Search Report for EP 06020836.0 date of completion is Feb. 13, 2007 (9 pages).

(Continued)

*Primary Examiner*—Brian D Nash

(57) ABSTRACT

A staple drive assembly includes an actuation sled and at least one staple pusher. The staple drive assembly is adapted to fit within a staple cartridge having a plurality of staples and a corresponding number of retention slots. The at least one staple pusher includes at least one pusher plate for releasably engaging a backspan of a staple. The staple pusher may include a plurality of pusher plates that may be laterally and longitudinally spaced apart. An actuation member has at least one angled camming surface for engaging a complimentary angled surface of the at least one staple pusher. Camming engagement between the actuation member and the at least one staple pusher causes vertical movement of the at least one staple pusher. Lateral and longitudinal offset of the actuation member camming surfaces and the corresponding staple pusher following surfaces improves stability and control of the staple pusher during firing.

9 Claims, 19 Drawing Sheets

U.S. PATENT DOCUMENTS

| | | | |
|---|---|---|---|
| 5,040,715 A | 8/1991 | Green et al. | |
| 5,156,315 A | 10/1992 | Green et al. | |
| 5,253,793 A | 10/1993 | Green et al. | |
| 5,312,023 A * | 5/1994 | Green et al. | 227/175.1 |
| 5,312,024 A * | 5/1994 | Grant et al. | 227/179.1 |
| 5,318,221 A * | 6/1994 | Green et al. | 227/178.1 |
| 5,364,001 A * | 11/1994 | Bryan | 227/175.1 |
| 5,364,003 A | 11/1994 | Williamson, IV | |
| 5,395,034 A * | 3/1995 | Allen et al. | 227/178.1 |
| 5,397,046 A | 3/1995 | Savage et al. | |
| 5,415,334 A | 5/1995 | Williamson, IV et al. | |
| 5,465,895 A | 11/1995 | Knodel et al. | |
| 5,487,500 A | 1/1996 | Knodel et al. | |
| 5,489,058 A | 2/1996 | Plyley et al. | |
| 5,535,935 A | 7/1996 | Vidal et al. | |
| 5,562,241 A | 10/1996 | Knodel et al. | |
| 5,571,116 A | 11/1996 | Bolanos et al. | |
| 5,586,711 A | 12/1996 | Plyley et al. | |
| 5,597,107 A | 1/1997 | Knodel et al. | |
| 5,630,540 A | 5/1997 | Blewett | |
| 5,630,541 A | 5/1997 | Williamson, IV et al. | |
| 5,662,258 A | 9/1997 | Knodel et al. | |
| 5,738,474 A | 4/1998 | Blewett | |
| 5,762,255 A | 6/1998 | Chrisman et al. | |
| 5,797,537 A | 8/1998 | Oberlin et al. | |
| 5,816,471 A | 10/1998 | Plyley et al. | |
| 5,820,009 A | 10/1998 | Melling et al. | |
| 6,010,054 A | 1/2000 | Johnson et al. | |
| 6,131,789 A * | 10/2000 | Schulze et al. | 227/175.4 |
| 6,669,073 B2 * | 12/2003 | Milliman et al. | 227/175.2 |
| 7,055,730 B2 | 6/2006 | Ehrenfels et al. | |
| 2002/0117533 A1 * | 8/2002 | Milliman et al. | 227/175.2 |
| 2004/0232200 A1 | 11/2004 | Shelton, IV et al. | |
| 2006/0016853 A1 | 1/2006 | Racenet | |
| 2007/0194079 A1 | 8/2007 | Hueil et al. | |

FOREIGN PATENT DOCUMENTS

| | | |
|---|---|---|
| EP | 0669104 | 8/1995 |
| EP | 1 772 105 A | 4/2007 |
| WO | WO 2004/032763 A2 | 4/2004 |
| WO | WO2004032763 | 4/2004 |

OTHER PUBLICATIONS

European Search Report for EP 08252860.5-2310 date of completion is Feb. 4, 2009 (3 pages).

* cited by examiner

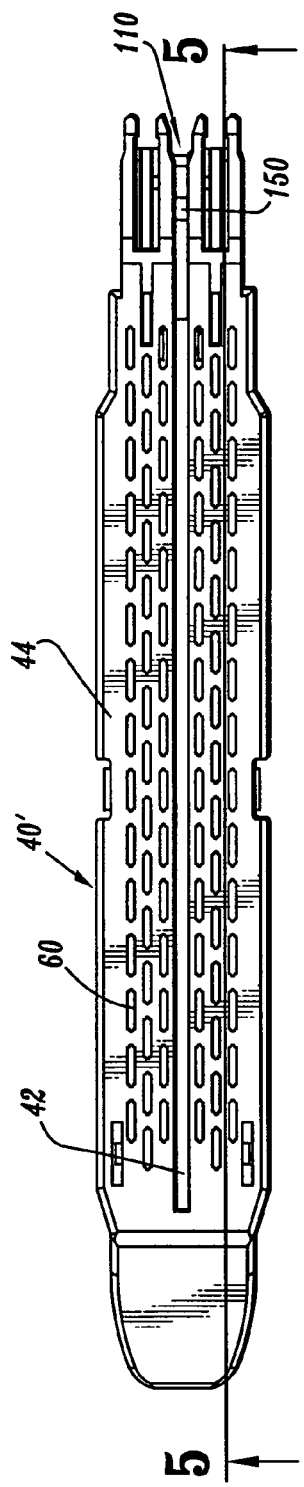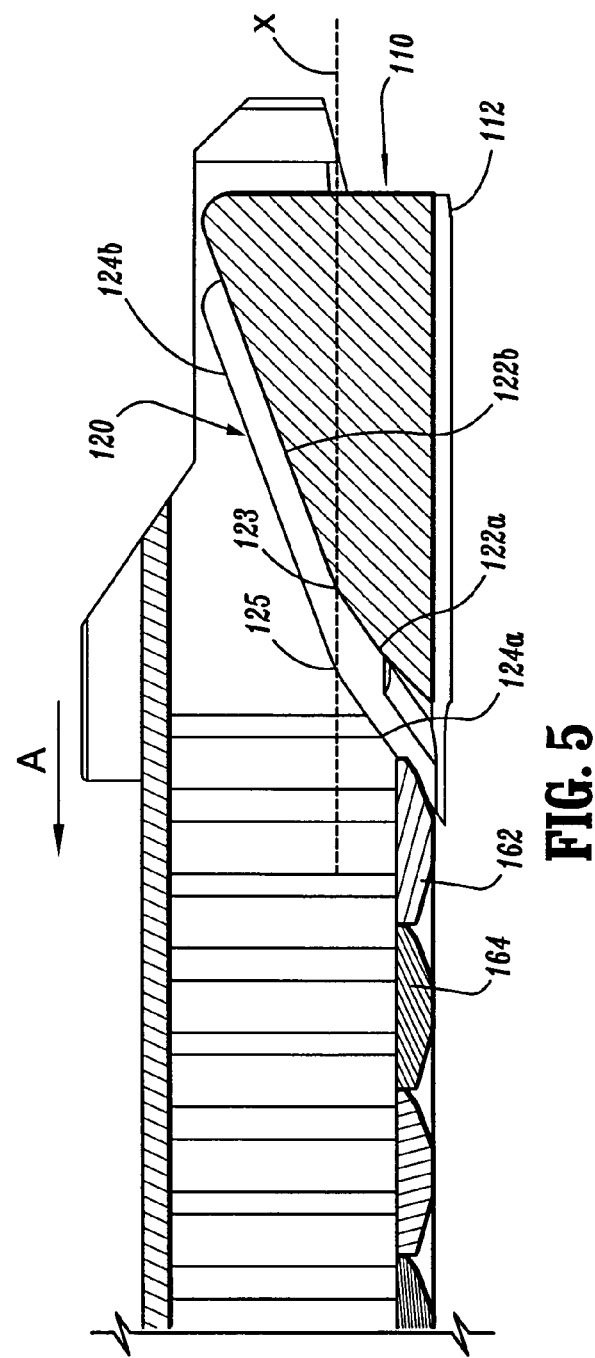
FIG. 4
FIG. 5

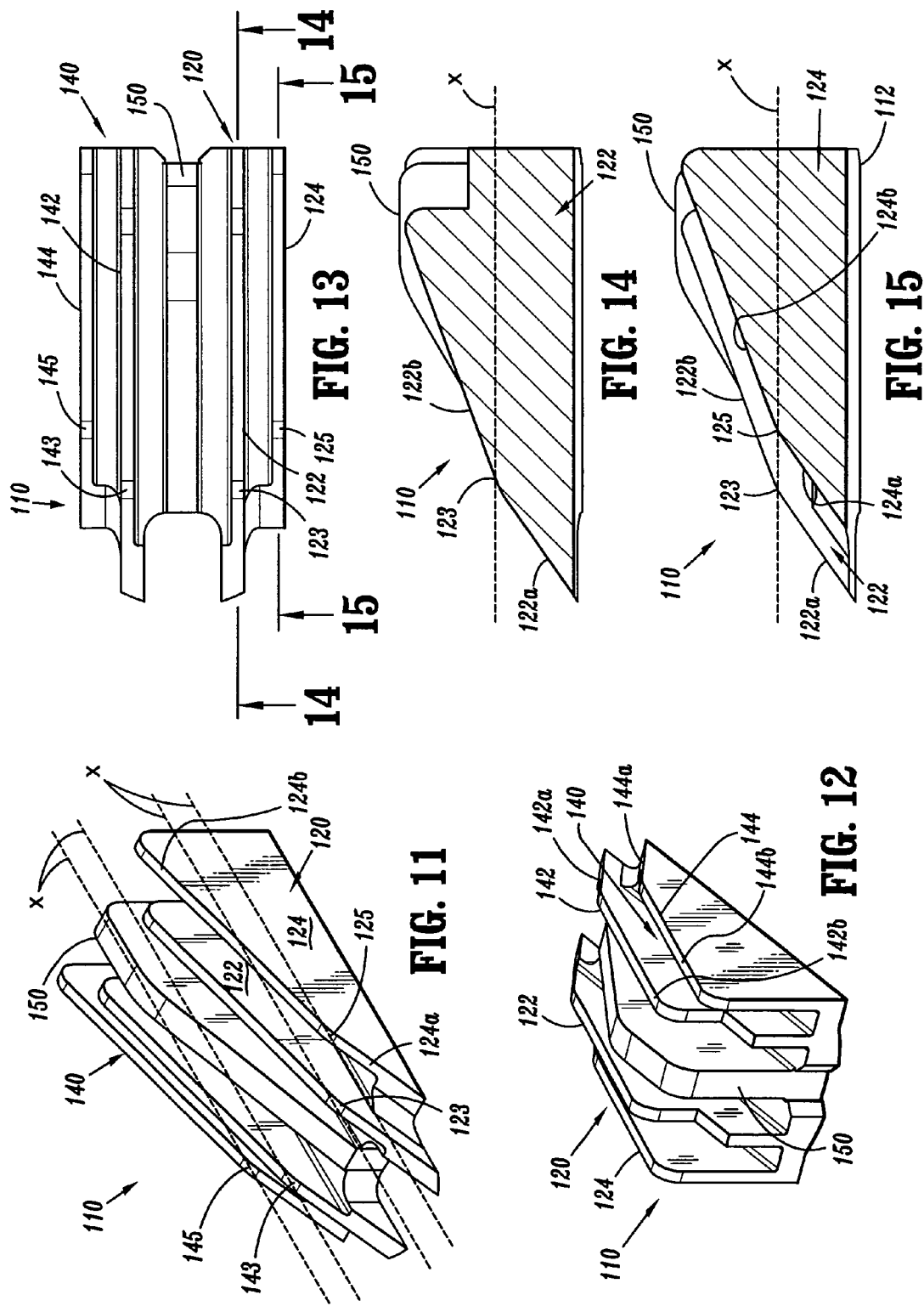

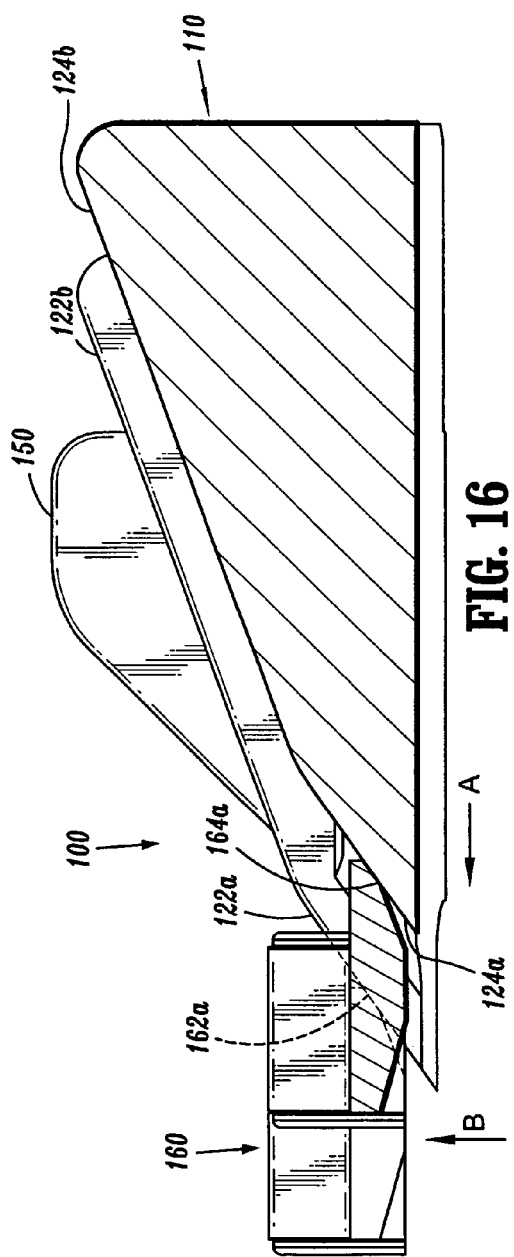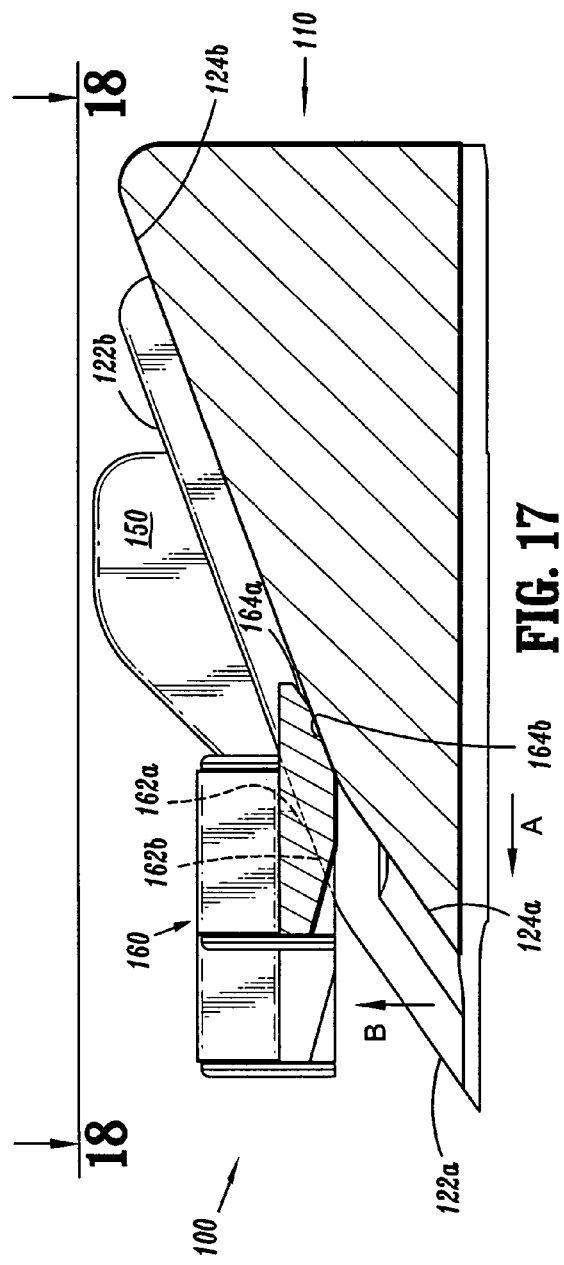
FIG. 16
FIG. 17

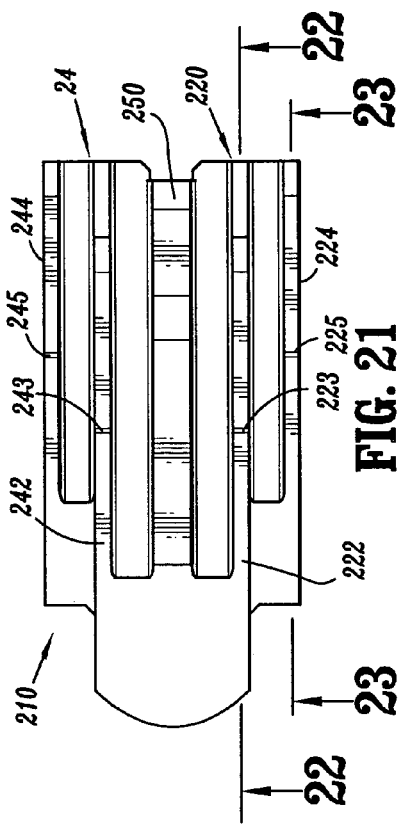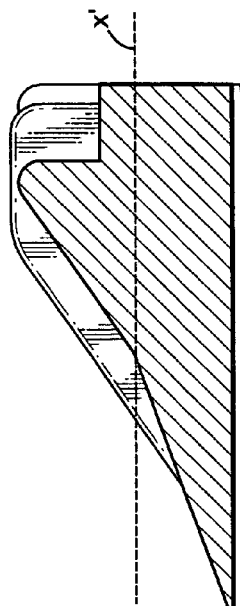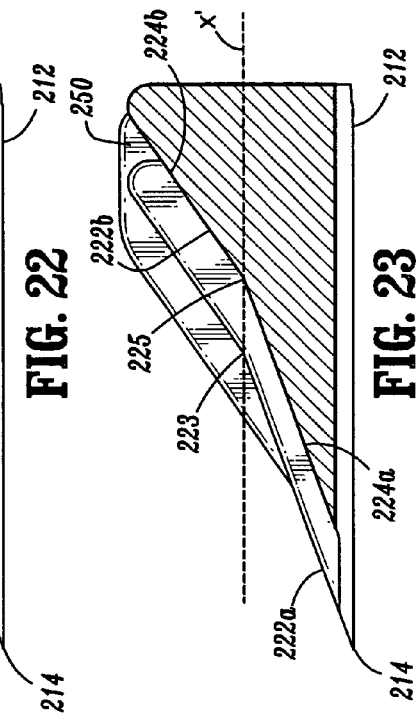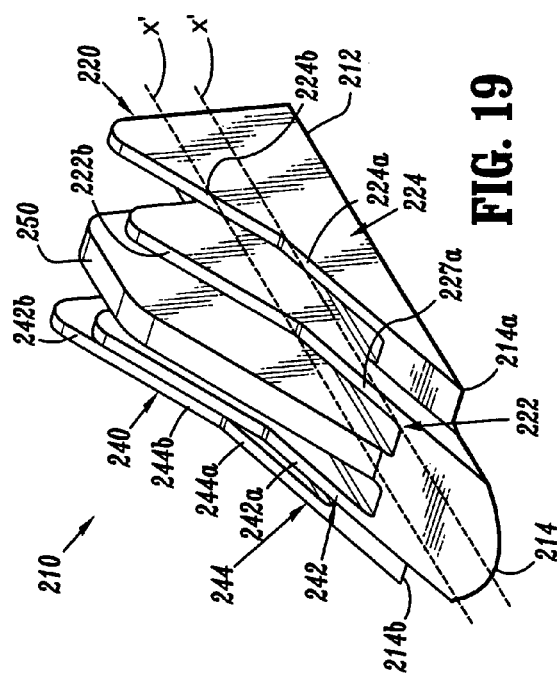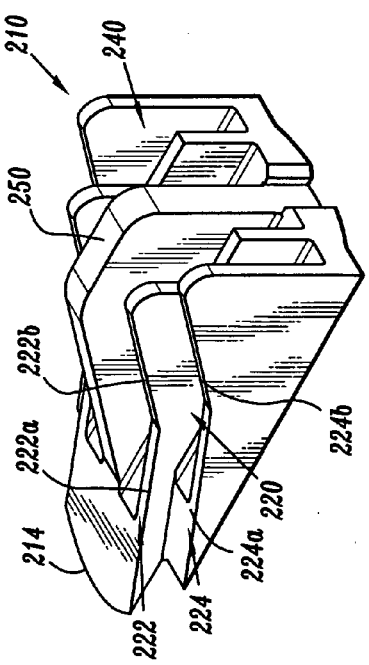

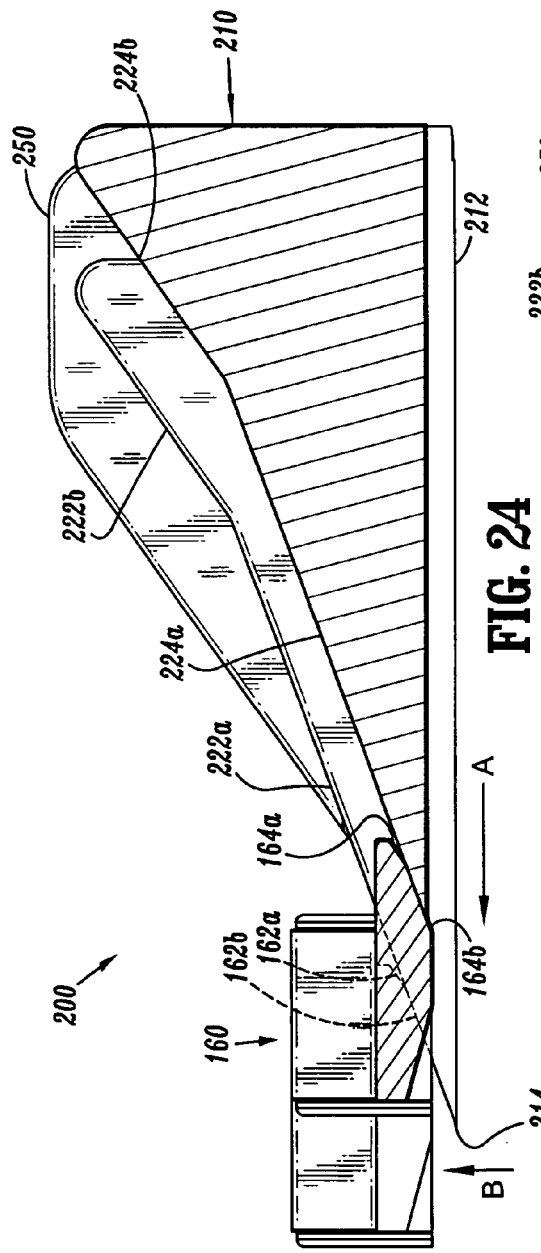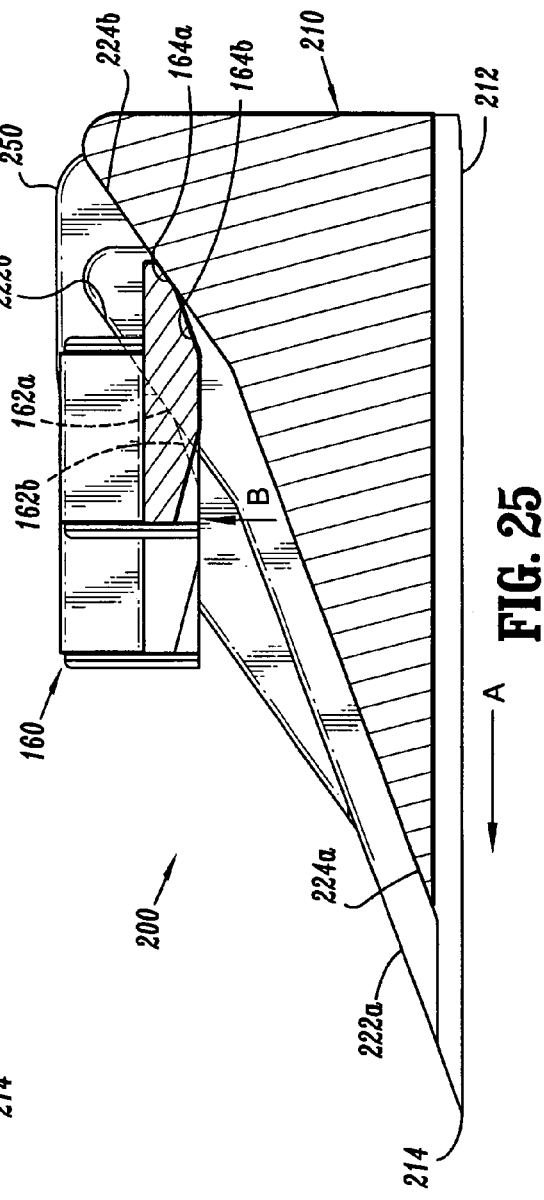

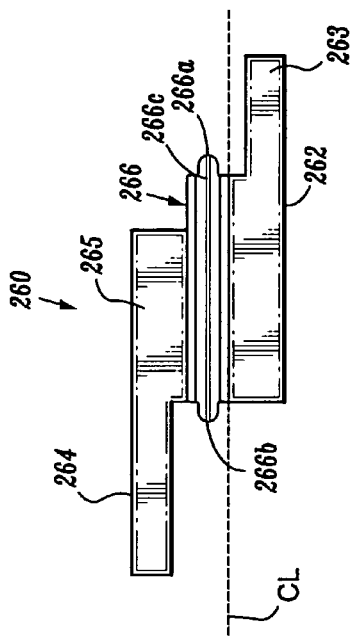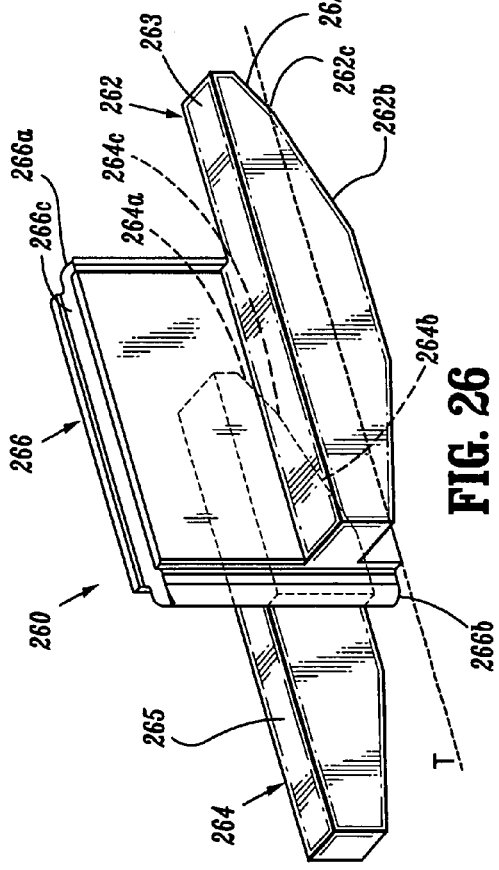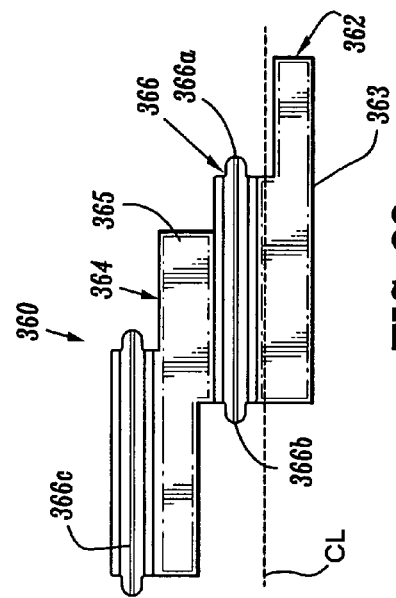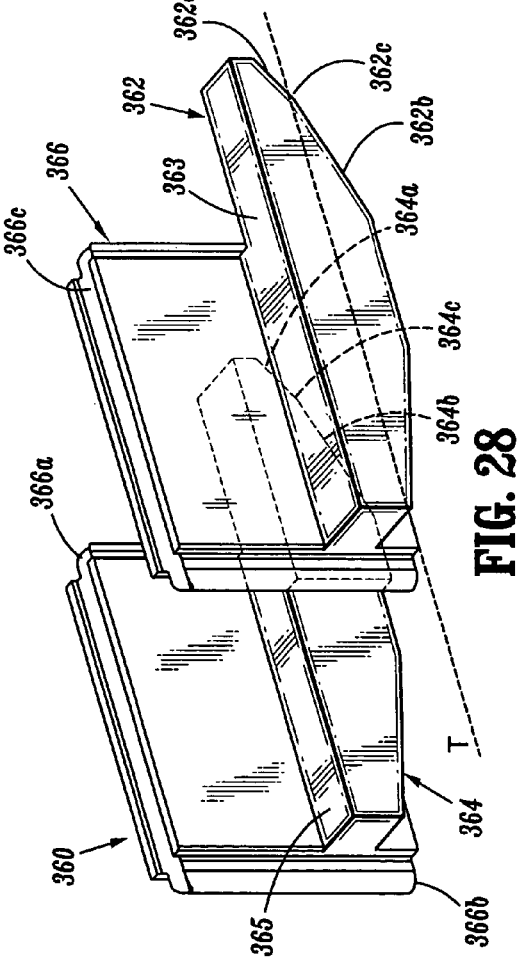

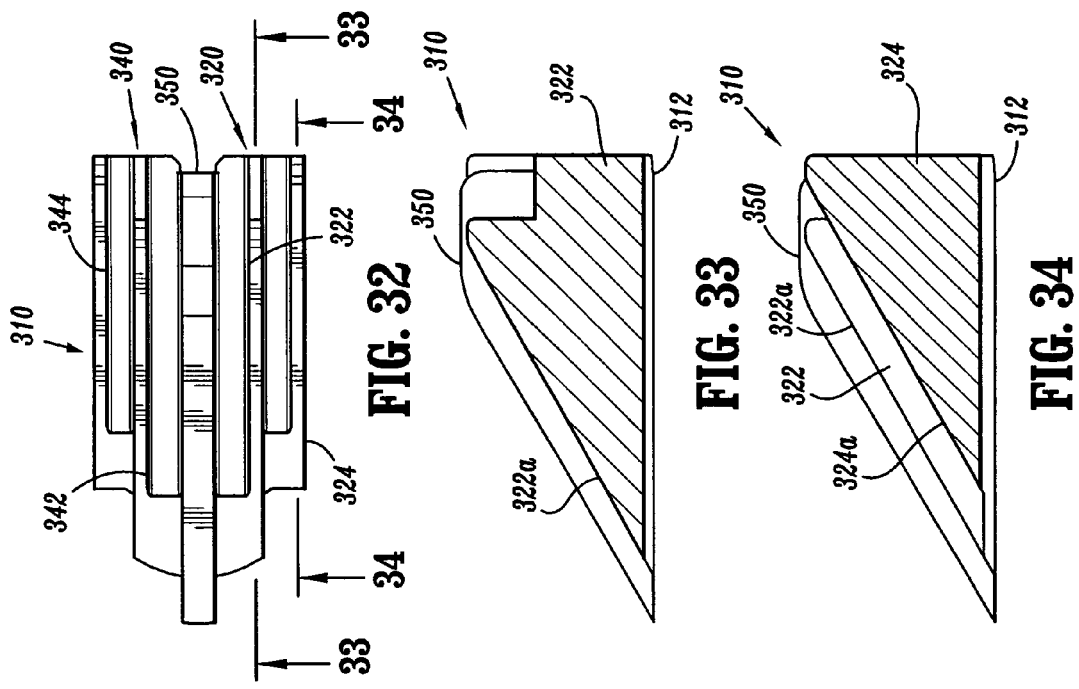
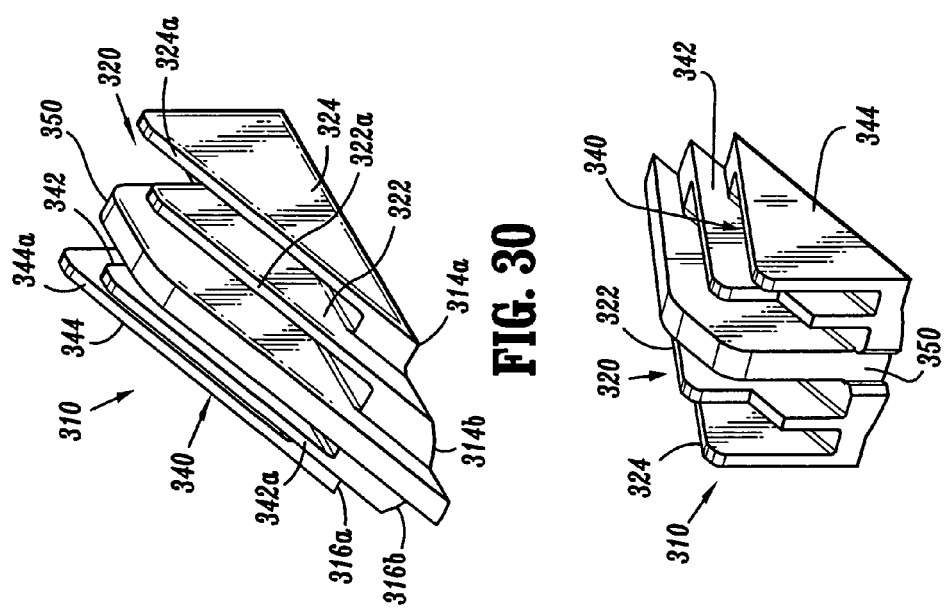

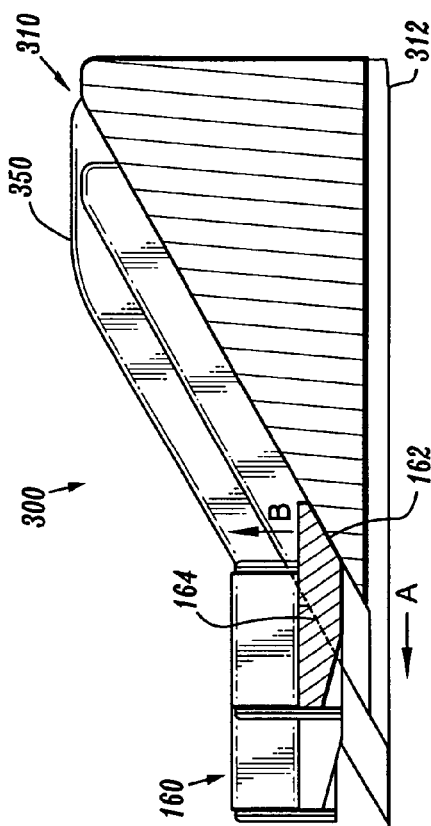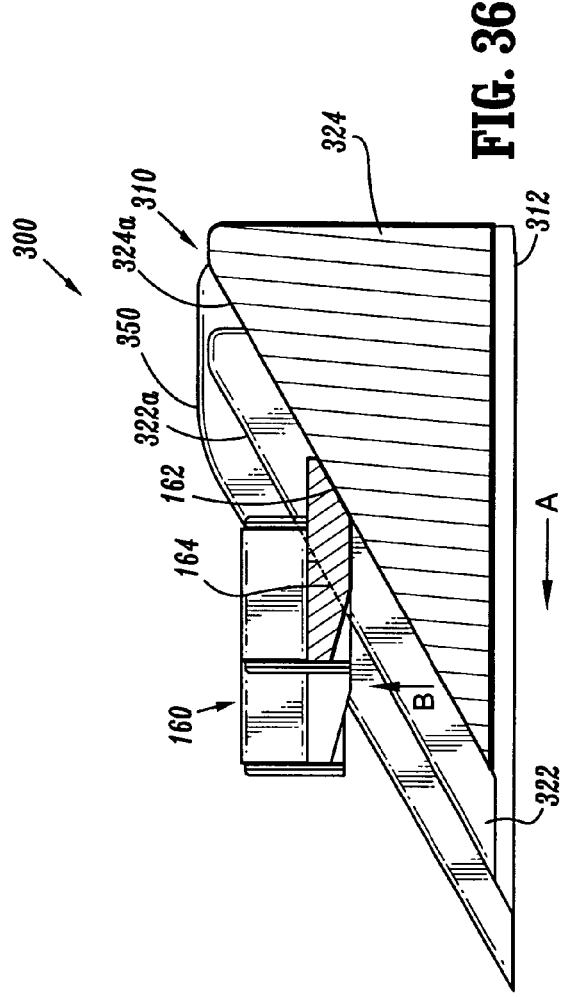

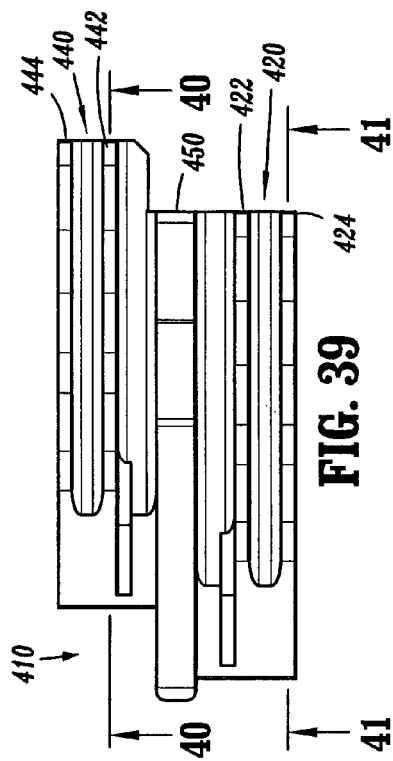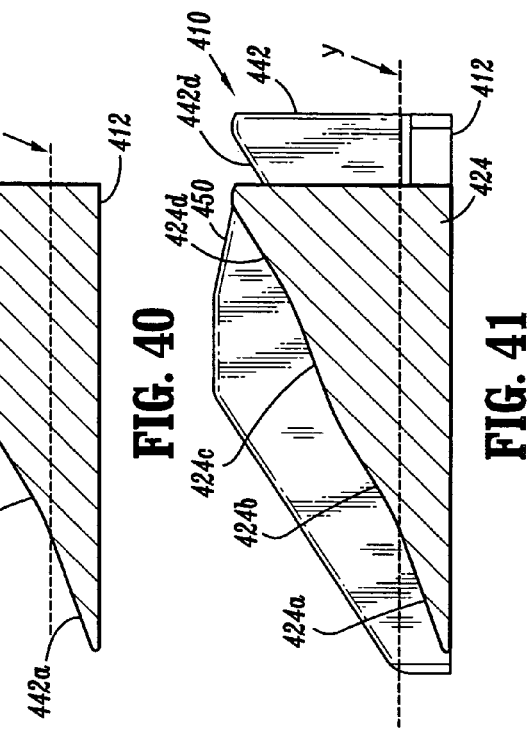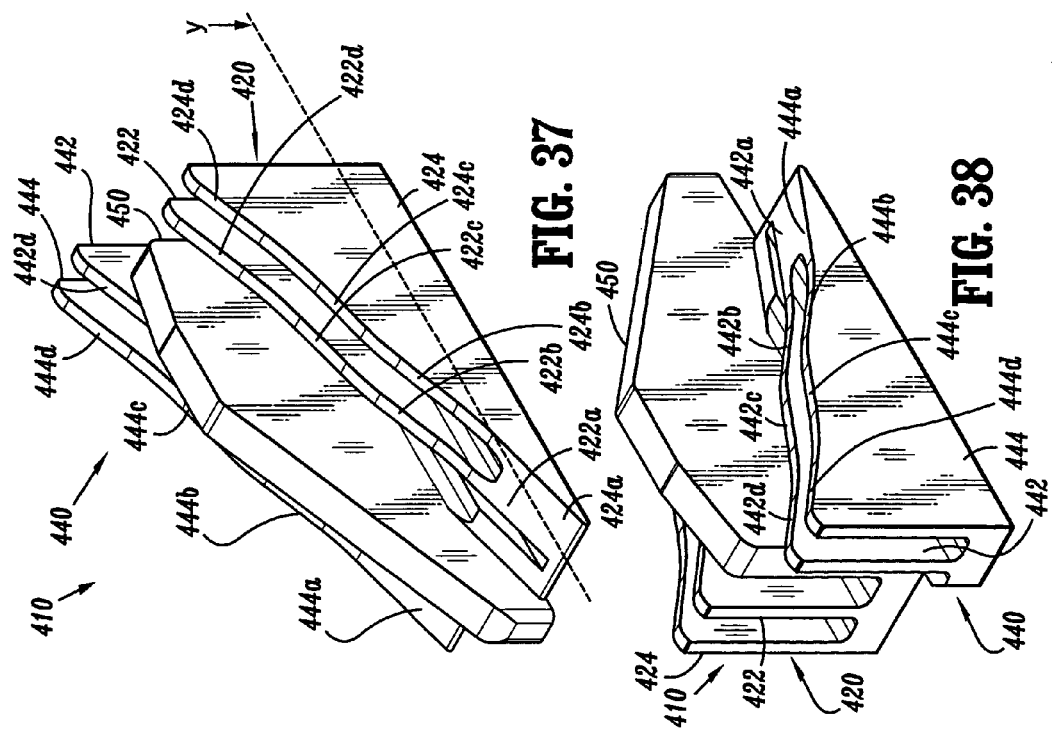

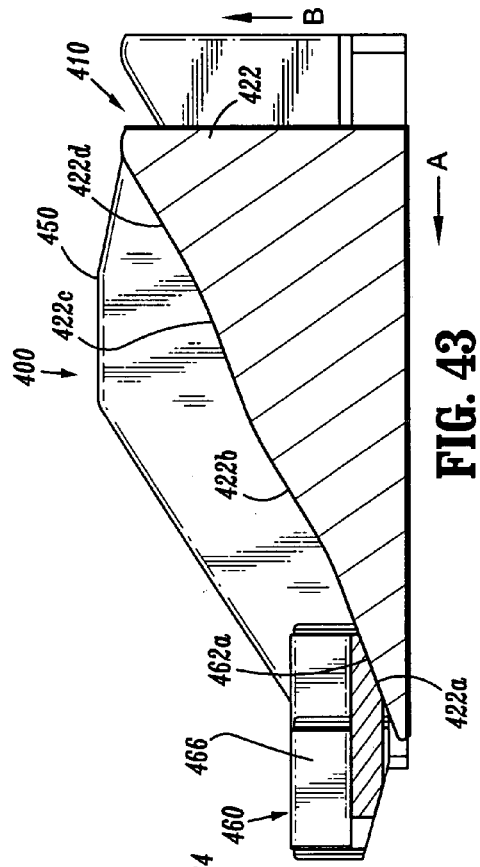
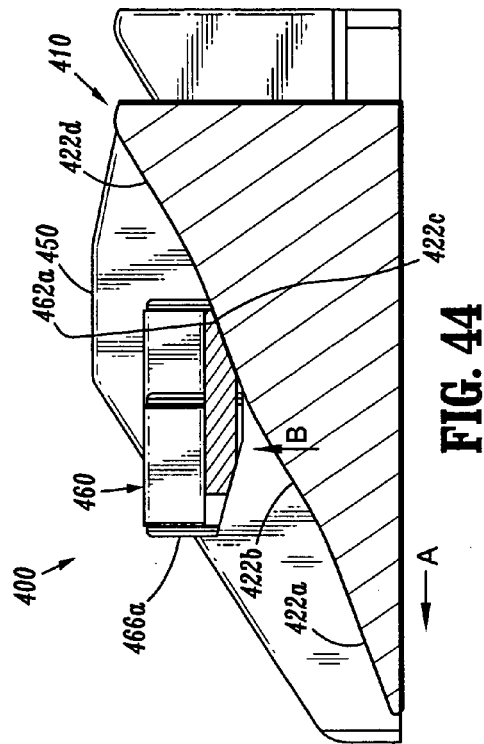
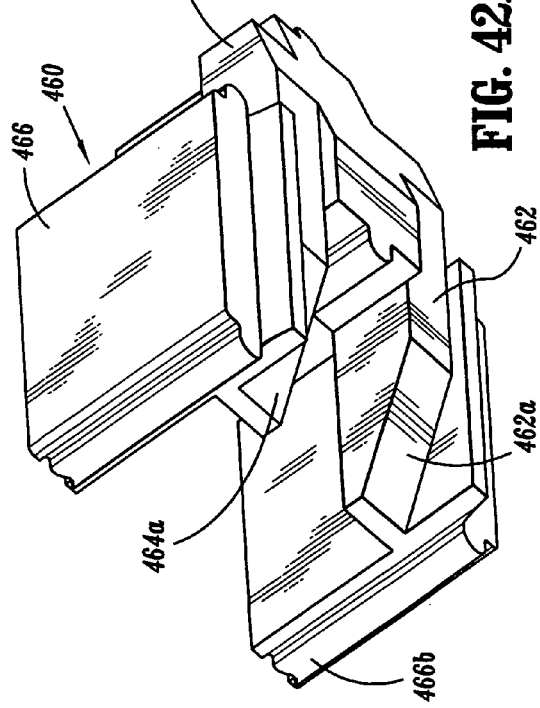
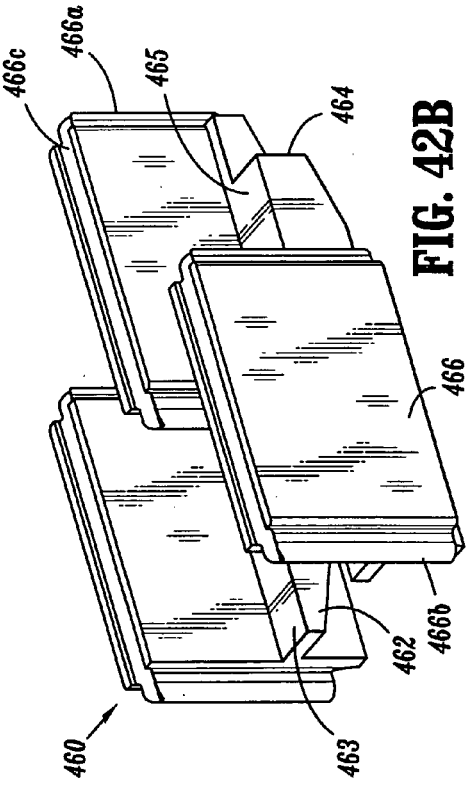

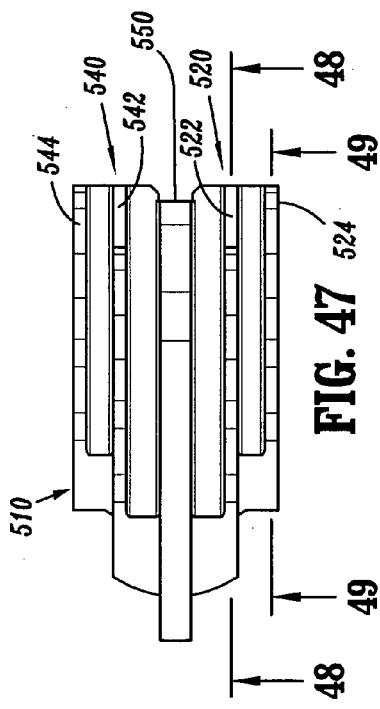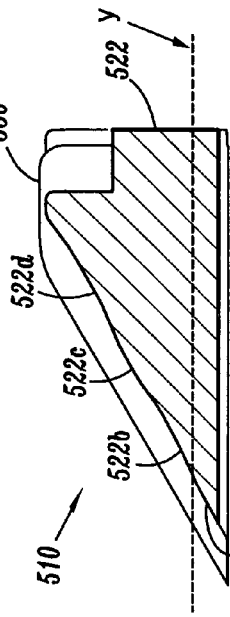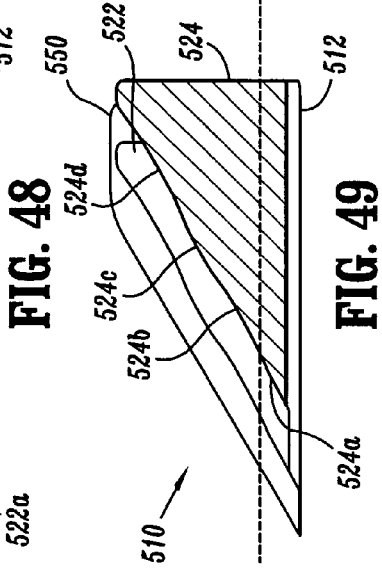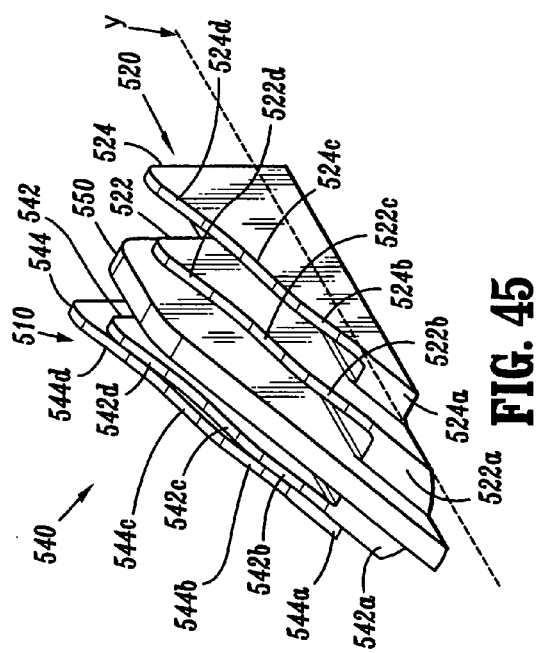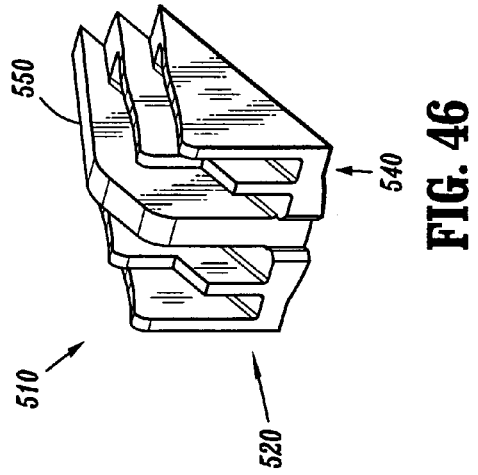

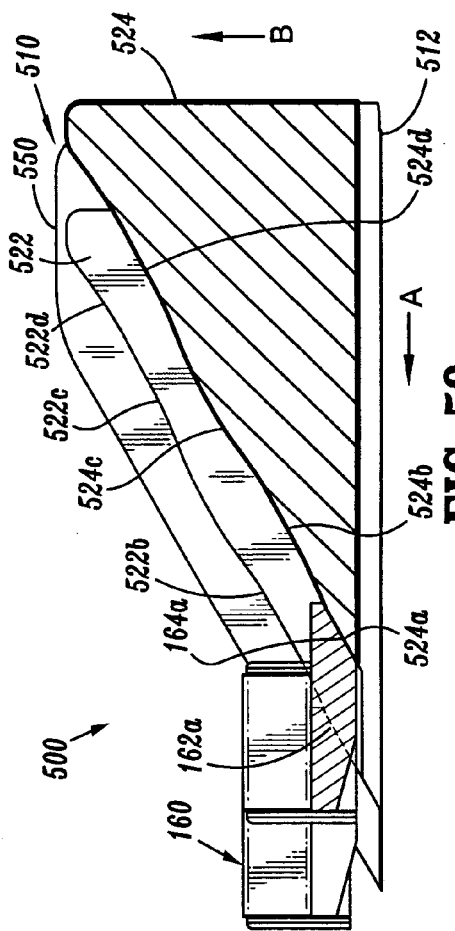
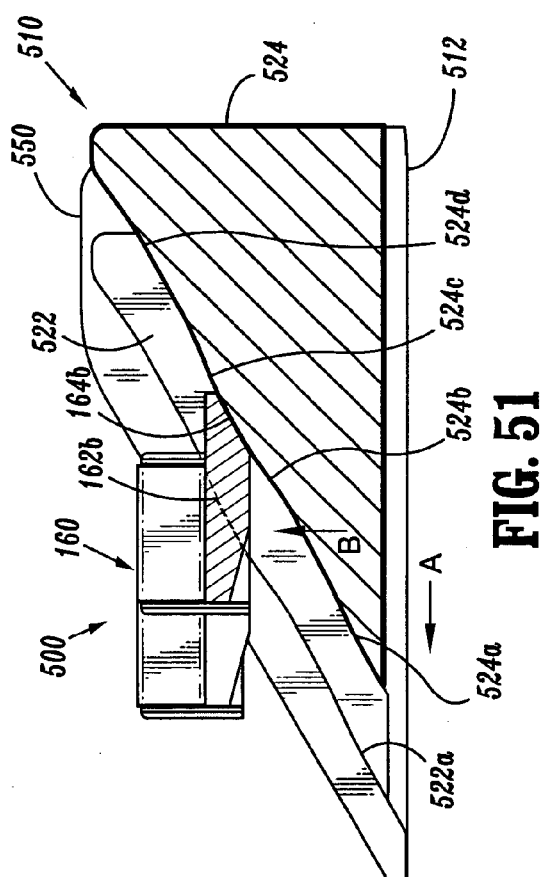

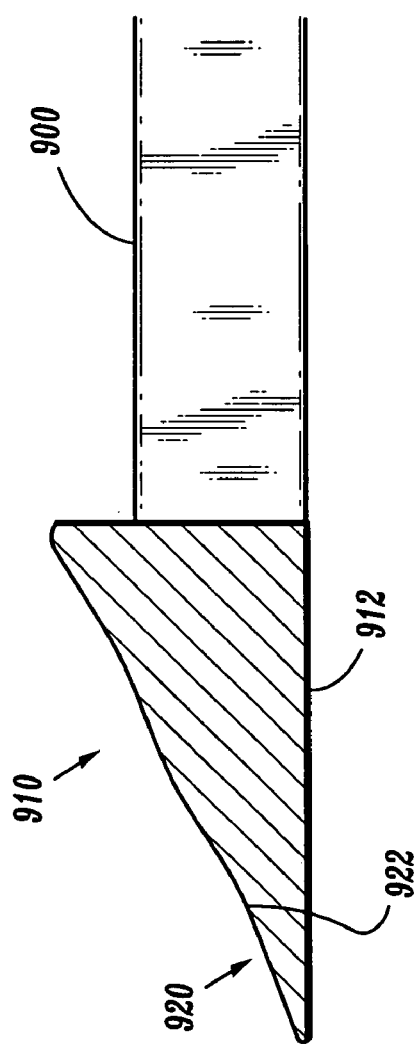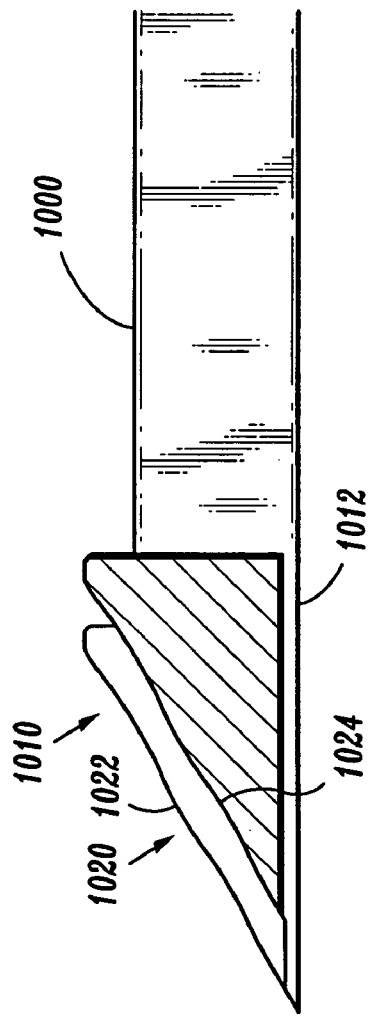

STAPLE DRIVE ASSEMBLY

BACKGROUND

1. Technical Field

The present disclosure relates to stapling apparatus. More particularly, the present disclosure relates to a staple drive assembly for use in a staple cartridge of a stapling apparatus.

2. Background of Related Art

Surgical stapling apparatus are widely used in surgical procedures to fasten body tissue quickly and efficiently by driving fasteners, or staples into the tissue. In certain types of stapling apparatus, a drive member moves transversely to the direction the staples are to be driven. Typically, such stapling apparatus employ a number of staple pusher elements located in grooved slots of a staple cartridge and arranged end to end in rows. Under normal operation, the transversely moving drive member contacts a cam member on the staple pusher thereby pushing the staple pusher vertically in the grooved slot. The staple pusher transmits linear motion from the drive member to the staples. The rows of staples are thereby driven into the body tissue to be fastened.

Several issues arise in designing staple pushers for driving one or more surgical staples. If the forces applied to the staple pusher are not effectively balanced, there is a tendency for the staple pusher to twist within the grooved slot and/or bind against the walls of the grooved slot. Additionally, a single point of contact between the actuation sled and the staple pusher may create a rocking point on the staple pusher which can cause the staple pusher to exit the staple cartridge in an unbalanced manner which may result in non-uniform staple formation. Moreover, staple pushers for driving a plurality of staples may offer more resistance to longitudinal movement of the drive member. It is desirable that the staple pusher permit application of a relatively smooth ejection force throughout the operation of the drive member. It is also desirable that the stapling apparatus form a plurality of finished staples having a substantially uniform configuration.

Various staple pusher and cam bar arrangements are known. See, for example, U.S. Pat. Nos. 4,955,959; 4,978,049; 5,395,034; 5,630,541; 5,662,258; 6,131,789 and D278,081.

SUMMARY

The present disclosure is directed towards a staple drive assembly for use in a staple cartridge. The staple drive assembly includes an actuation sled and at least one staple pusher. The staple cartridge includes a tissue contacting surface having a number of retention slots wherein each retention slot is adapted for releasably receiving a staple. The staple cartridge may include a guide channel extending from a proximal portion to a distal portion along its longitudinal axis. In one embodiment, the staple cartridge is adapted for use in a surgical stapler having a drive mechanism.

The actuation sled includes a base, at least one camming member and a guide member. Each camming member includes a first or leading cam wedge and a second or trailing cam wedge. The leading and trailing cam wedges are laterally and longitudinally spaced apart from one another. Spacing of the cam wedges apart, both laterally and longitudinally, creates a situation in which the staple pusher is contacted at points offset in two planes so that as the staple pusher is driven, it is controlled and driven substantially perpendicular to the tissue plane of the cartridge without rocking in any direction which would compromise driving the staple perpendicular to the tissue contacting plane. Additionally, each cam wedge includes a first drive face and a second drive face. In one embodiment, the first drive faces form first drive angles with respect to the base and second drive faces form second drive angles with respect to a plane that is substantially parallel to the base. The guide member is adapted for slidably engaging the guide channel for aligning and guiding the actuation sled as it translates through the staple cartridge. In one embodiment, first drive faces are oriented such that first drive angles may be in a range of about 30° to about 40° while the second drive faces are oriented such that second drive angles may be in a range of about 15° to about 25°.

Each staple pusher includes at least one pusher plate and at least one cam member. In one embodiment, each staple pusher includes three pusher plates and two cam members. In an alternate embodiment, each staple pusher includes one pusher plate and two cam members. In a further embodiment, each staple pusher includes two pusher plates and two cam members. First and second cam members are adapted for slidably engaging one of the cam assemblies of the actuation sled. Each cam member includes first and second cam surfaces that define respective first and second engagement or receiving angles that are complementary to the first and second drive angles. In one embodiment, the first receiving angles may be in a range of about 15° to about 55° while the second receiving angles may be in a range of about 5° to about 35°. In another embodiment, the first receiving angles may be in a range of about 25° to about 45° while the second receiving angles may be in a range of about 10° to about 30°. In a further embodiment, the first receiving angle may be in the range of about 30° to about 40° while the second receiving angle may be in the range of about 15° to about 25°. The first and second cam members are longitudinally and laterally spaced apart to complement the arrangement of the leading and trailing cam wedges of the actuation sled.

Distal travel of the actuation sled through the staple cartridge causes the sequential engagement of the actuation sled and the staple pushers disposed in the staple cartridge. As the actuation sled moves along the longitudinal axis of the staple cartridge, the first drive faces slidably engage the first cam surfaces thereby urging each staple pusher in a generally vertical direction. As the actuation sled continues to move distally, the second drive faces slidably engage the second cam surfaces of each staple pusher to continue to drive each staple pusher in a generally vertical direction while the first drive faces disengage from the first cam surfaces. Each camming member contacts each staple pusher in at least two longitudinally spaced locations for urging each staple pusher vertically. This longitudinally staggered arrangement of the drive faces in cooperation with the complementary staggered arrangement of the cam members maximizes the longitudinal stability of the staple pusher as it moves vertically. Additionally, the first and second drive angles in cooperation with the complementary first and second receiving angles contribute to the improved longitudinal stability of each staple pusher.

In another embodiment of the present disclosure, an actuation sled includes substantially the same or similar components, but the first and second drive angles may be in a range of about 5° to about 35° while the second drive angles may be in a range of about 20° to about 55°. In another embodiment, first drive angles may be in a range of about 10° to about 30° while second drive angles may be in a range of about 25° to about 45°. In a further embodiment, first drive angles may be in a range of about 15° to about 25° while second drive angles may be in a range of about 30° to about 40°. During distal movement of the actuation sled, the first drive faces slidably engage the second cam surfaces urging each staple pusher in a generally vertical direction. As the actuation sled continues to move distally, the second drive faces engage first cam surfaces as the first drive faces disengage from the second cam surfaces. Applicants have found that providing a cam wedges with a first drive surface angle which is less than the second drive angle provides a smooth firing stroke. Similar to the previous embodiment, longitudinal stability of the staple pusher is maximized by the longitudinally staggered (i.e. spaced apart) cam members in cooperation with the complementarily staggered cam wedges. In addition, when the first drive angle is less than the second drive angle, the staple pusher contacts both drive surfaces as contact with the staple pusher transitions from contacting one drive surface to the other drive surface.

In a further embodiment of the present disclosure, an actuation sled is disclosed that includes the same or substantially similar components. In this embodiment, the actuation sled includes first and second camming members, a base, and a guide member. Each camming member further includes first and second cam wedges that are longitudinally spaced apart and define a drive angle with respect to the base. The first and second cam wedges of each camming member are laterally spaced apart as well.

Another embodiment of the present disclosure includes an actuation sled that has the same or substantially similar components. According to this embodiment, the actuation sled includes first and second camming members, a base, and a guide member. Each camming member further includes first and second cam wedges that are laterally spaced apart from each other and define a plurality of drive angles with respect to the base. In particular, each cam wedge defines a first set of drive angles that may be in the range of about 15° to about 25° and a second set of drive angles that may be in the range of about 26° to about 36°. In another embodiment, each cam wedge defines a first set of drive angles that may be in the range of about 17° to about 23° and a second set of drive angles that may be in the range of about 28° to about 34°. In a further embodiment, each cam wedge defines a first set of drive angles that may be in the range of about 19° to about 21° and a second set of drive angles that may be in the range of about 30° to about 32°.

In an alternate embodiment of the present disclosure, an actuation sled is described having the same or substantially similar components. According to this embodiment, the actuation sled includes first and second camming members, a base, and a guide member. Each camming member further includes first and second cam wedges that are laterally and longitudinally spaced apart from each other and define a plurality of drive angles with respect to the base. In particular, each cam wedge defines a first set of drive angles that may be in the range of about 15° to about 55° and a second set of drive angles that may be in the range of about 5° to about 35°. In another embodiment, each cam wedge defines a first set of drive angles that may be in the range of about 25° to about 45° and a second set of drive angles that may be in the range of about 10° to about 30°. In a further embodiment, each cam wedge defines a first set of drive angles that may be in the range of about 30° to about 40° and a second set of drive angles that may be in the range of about 10° to about 30°.

In yet another embodiment of the present disclosure, each of the described actuation sleds may be included at a distal end of a cam bar or actuation member in a surgical stapling apparatus.

As will be appreciated from the disclosure, controlled driving of the staple pushers can be maximized by providing cam wedges which are offset both laterally and longitudinally from each other with each drive surface having a first drive angle which is less than the second drive angle.

BRIEF DESCRIPTION OF THE DRAWINGS

Embodiments of the presently disclosed staple drive assembly are described herein with reference to the drawings, wherein:

FIG. 4 is a top plan view of the staple cartridge of FIG. 4 with the actuation sled in an initial position;

FIG. 5 is a side cross-sectional view of a proximal portion of the staple cartridge taken along section line 5-5 of FIG. 4;

FIG. 11 is a front perspective view of the actuation sled of FIG. 1;

FIG. 12 is a rear perspective view of the actuation sled of FIG. 1;

FIG. 13 is a top plan view of the actuation sled of FIG. 1;

FIG. 14 is a side cross-sectional view taken along section line 14-14 of FIG. 13;

FIG. 15 is a side cross-sectional view taken along section line 15-15 of FIG. 13;

FIG. 16 is a side cross-sectional view of the staple drive assembly of FIG. 1 showing the initial engagement between the cam members of the staple pusher of FIG. 6 and the cam wedges of the actuation sled as the actuation sled moves in the direction of arrow A;

FIG. 17 is a side cross-sectional view of the staple drive assembly of FIG. 1 showing the continued engagement between the cam members of the staple pusher of FIG. 6 and the cam wedges of the actuation sled as the actuation sled continues to move in the direction of arrow A;

FIG. 19 is a front perspective view of an actuation sled according to another embodiment of the present disclosure;

FIG. 20 is a rear perspective view of the actuation sled of FIG. 19;

FIG. 21 is a top plan view of the actuation sled of FIG. 19;

FIG. 22 is a side cross-sectional view of the actuation sled of FIG. 19 taken along section line 21-21 of FIG. 21;

FIG. 23 is a side cross-sectional view of the actuation sled of FIG. 19 taken along section line 23-23 of FIG. 21;

FIG. 24 is a side cross-sectional view of another embodiment of a staple drive assembly including the actuation sled of FIG. 19 showing the initial engagement between the cam members of the staple pusher of FIG. 6 and the cam wedges of the actuation sled as the actuation sled moves in the direction of arrow A;

FIG. 25 is a side cross-sectional view of the staple drive assembly of FIG. 24 showing the continued engagement between the cam members of the staple pusher of FIG. 6 and the cam wedges of the actuation sled as the actuation sled continues to move in the direction of arrow A;

FIG. 26 is a rear perspective view of an alternate embodiment of a staple pusher in accordance with the present disclosure;

FIG. 27 is a top plan view of the staple pusher of FIG. 26;

FIG. 28 is a rear perspective view of another embodiment of a staple pusher in accordance with the present disclosure;

FIG. 29 is a top plan view of the staple pusher of FIG. 28;

FIG. 30 is a front perspective view of an actuation sled according to another embodiment of the present disclosure;

FIG. 31 is a rear perspective view of the actuation sled of FIG. 30;

FIG. 32 is a top plan view of the actuation sled of FIG. 30;

FIG. 33 is a side cross-sectional view taken along section line 33-33 of FIG. 32;

FIG. 34 is a side cross-sectional view taken along section line 34-34 of FIG. 32;

FIG. 35 is a side cross-sectional view of another embodiment of a staple drive assembly including the actuation sled of FIG. 30 showing the initial engagement between the cam members of the staple pusher of FIG. 6 and the cam wedges of the actuation sled as the actuation sled moves in the direction of arrow A;

FIG. 36 is a side cross-sectional view of the staple drive assembly of FIG. 35 showing the continued engagement between the cam members of the staple pusher of FIG. 6 and the cam wedges of the actuation sled as the actuation sled continues to move in the direction of arrow A;

FIG. 37 is a front perspective view of an actuation sled according to another embodiment of the present disclosure;

FIG. 38 is a rear perspective view of the actuation sled of FIG. 37;

FIG. 39 is a top plan view of the actuation sled of FIG. 37;

FIG. 40 is a side cross-sectional view of the actuation sled of FIG. 39 taken along section lines 40-40 of FIG. 39;

FIG. 41 is a side cross-sectional view of the actuation sled of FIG. 39 taken along section line 41-41 of FIG. 39;

FIG. 42A is bottom perspective view of a pusher member according to an embodiment of the present disclosure;

FIG. 42B is side perspective view of the pusher member of FIG. 42A;

FIG. 43 is a side cross-sectional view of another embodiment of a staple drive assembly including the actuation sled of FIG. 37 showing the initial engagement between the cam members of the staple pusher of FIG. 42A and the cam wedges of the actuation sled as the actuation sled moves in the direction of arrow A;

FIG. 44 is a side cross-sectional view of the staple drive assembly of FIG. 43 showing the continued engagement between the cam members of the staple pusher of FIG. 42A and the cam wedges of the actuation sled as the actuation sled continues to move in the direction of arrow A;

FIG. 45 is a front perspective view of an actuation sled according to another embodiment of the present disclosure;

FIG. 46 is a rear perspective view of the actuation sled of FIG. 45;

FIG. 47 is a top perspective view of the actuation sled of FIG. 45;

FIG. 48 is a side cross-sectional view of the actuation sled of FIG. 47 taken along section lines 48-48 of FIG. 47;

FIG. 49 is a side cross-sectional view of the actuation sled of FIG. 47 taken along section lines 49-49 of FIG. 47;

FIG. 50 is a side cross-sectional view of another embodiment of a staple drive assembly including the actuation sled of FIG. 45 showing the initial engagement between the cam members of the staple pusher of FIG. 6 and the cam wedges of the actuation sled as the actuation sled moves in the direction of arrow A;

FIG. 51 is a side cross-sectional view of the staple drive assembly of FIG. 50 showing the continued engagement between the cam members of the staple pusher of FIG. 6 and the cam wedges of the actuation sled as the actuation sled continues to move in the direction of arrow A;

FIG. 55 is a side cross-sectional view of an end portion of an actuation member according to a further embodiment of the present disclosure; and FIG. 56 is a side cross-sectional view of an end portion of an actuation member according to another embodiment of the present disclosure.

DETAILED DESCRIPTION OF THE PREFERRED EMBODIMENTS

Figure 1:
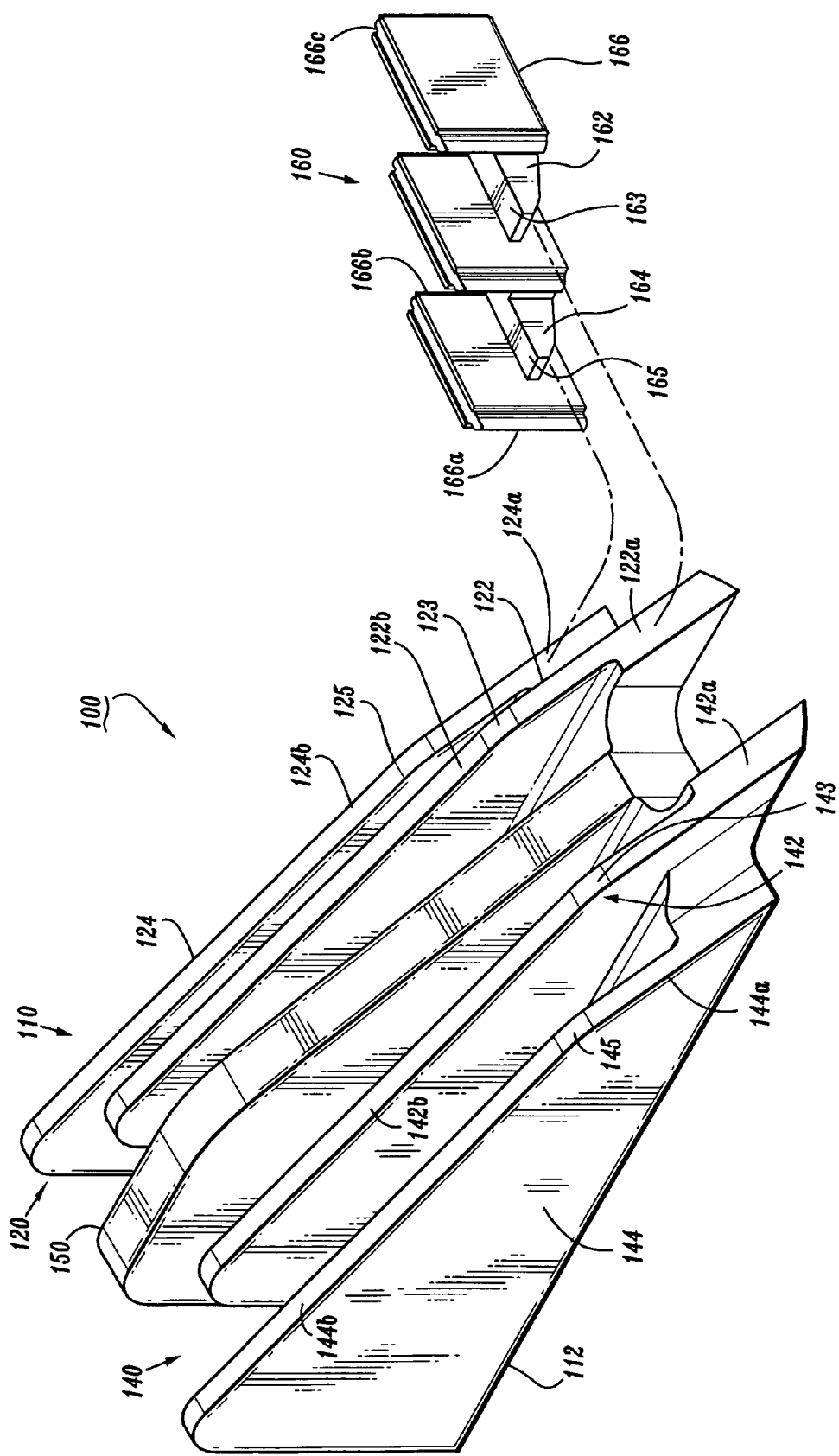
FIG. 1 is a perspective view of a staple drive assembly showing an actuation sled and a staple pusher in accordance with an embodiment of the present disclosure.

Embodiments of the presently disclosed staple drive assembly will now be described in detail with reference to the drawings, in which like reference numerals designate identical or corresponding elements in each of the several views. As used herein, the term "distal" refers to that portion of the instrument, or component thereof which is further from the user while the term "proximal" refers to that portion of the instrument or component thereof which is closer to the user.

A staple drive assembly 100, in accordance with one embodiment of the present disclosure, is illustrated in FIG. 1. Staple drive assembly 100 includes an actuation sled 110 and at least one staple pusher 160. Actuation sled 110 includes a base 112, a first camming member 120, a second camming member 140, and a guide member 150. First and second camming members 120, 140 include respective first or leading cam wedges 122, 142 and respective second or trailing cam wedges 124, 144. In one embodiment, staple drive assembly 100 is adapted for use in a surgical stapler having at least two linear rows of staples such as an endoscopic or laparoscopic stapler.

Figure 2:
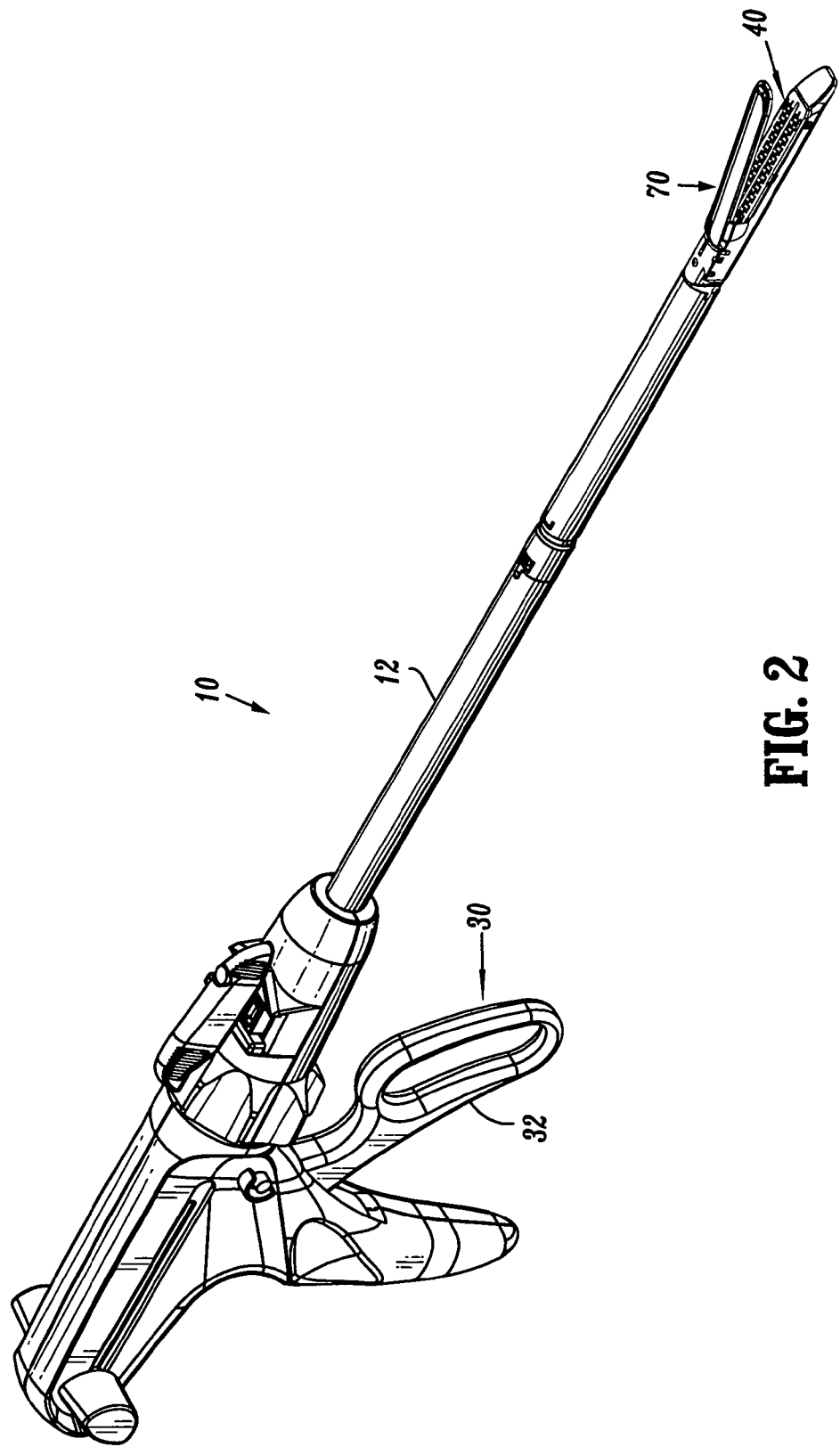
FIG. 2 is a perspective view of an endoscopic surgical stapling apparatus.

An example of a surgical stapler having linear rows of staples is disclosed in U.S. Pat. No. 6,669,073 to Milliman et al. currently owned and assigned to United States Surgical, the entire contents of which are incorporated herein by reference. As illustrated in FIG. 2, the surgical stapler is shown generally as 10. Surgical stapler 10 includes a trigger assembly 30, a body portion 12, a staple cartridge 40, and an anvil assembly 70. Trigger assembly 30 includes a pivotal trigger 32. Pivotal movement of trigger 32 during an actuation sequence of trigger 32 translates pivotal movement of trigger 32 into linear movement of a drive mechanism (not shown). The drive mechanism is operatively coupled to an actuation sled in staple cartridge 40 to translate linear movement of the drive mechanism to linear movement of the actuation sled. Stapler 10 is movable such that a portion of body tissue (not shown) may be positioned between anvil assembly 70 and staple cartridge 40. Actuation of stapler 10 moves anvil assembly 70 towards staple cartridge 40 thereby grasping or retaining the portion of body tissue therebetween. In addition, once the portion of body tissue is grasped between anvil assembly 70 and staple cartridge 40, continued actuation of stapler 10 discharges staples 50 (FIG. 3) through the portion of body tissue and against anvil assembly 70 to form completed staples 50. The presently disclosed staple drive assembly 100 may be incorporated into staple cartridge 40 of surgical stapler 10 disclosed in U.S. Pat. No. 6,669,073. Alternately, staple drive assembly 100 may be incorporated into other known stapling devices including open-type surgical stapling devices, such as the open surgical staplers shown and described U.S. Pat. Nos. 4,955,959; 4,978,049; 5,395,034; 5,630,541; 5,662,258; 6,131,789 and D278,081 and other endoscopic or laparoscopic surgical stapling devices, such as the endoscopic staplers shown and described in published U.S. Patent Applications 2004/0232195; 2004/0232197 and 2004/0232199. While the present disclosure describes embodiments involving an actuation sled, it also will be appreciated that the design characteristics and function of the sled camming members may be incorporated directly into cam bars or firing wedges, which in turn are connected to the firing mechanism of the surgical stapling instrument.

Figure 3:
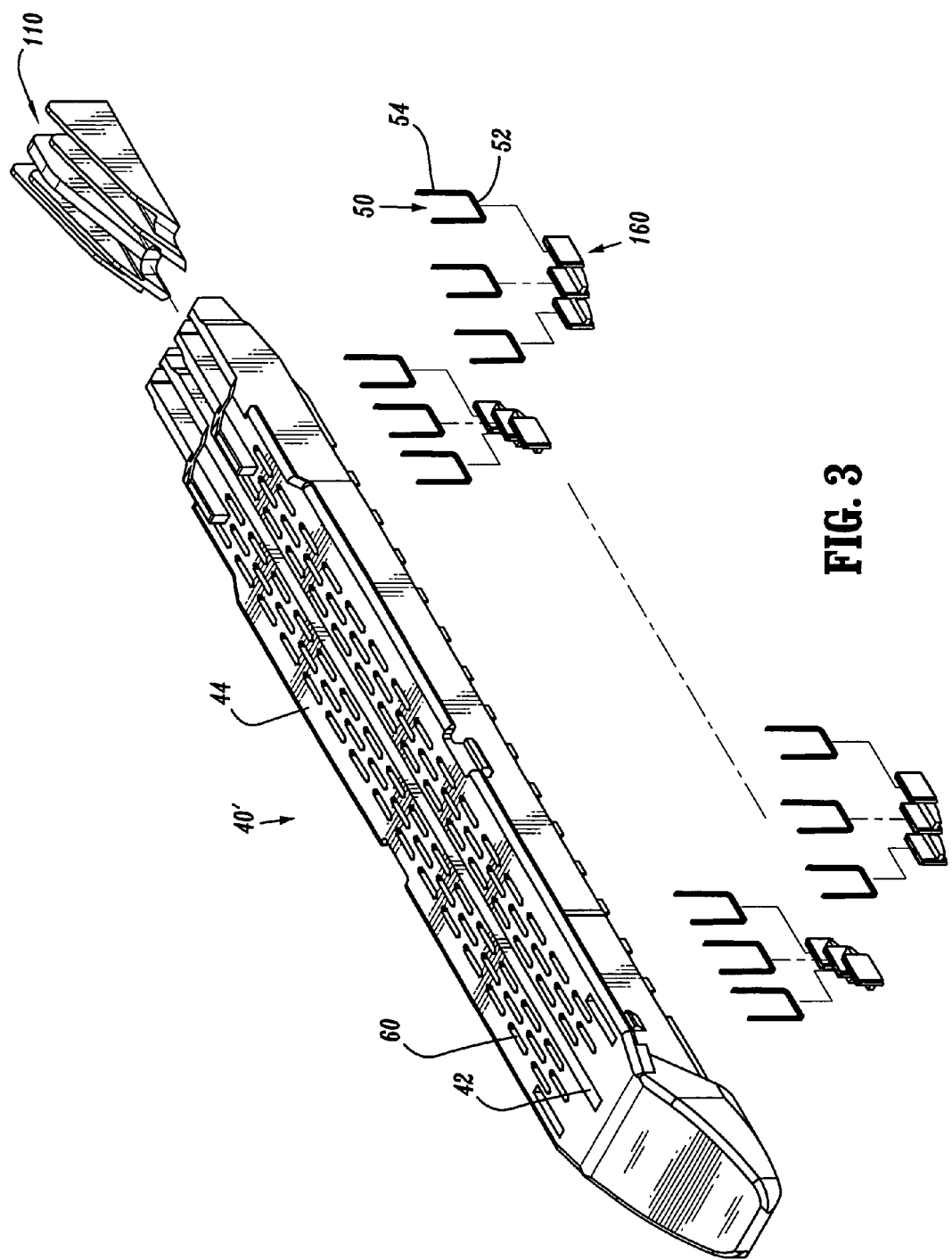
FIG. 3 is an exploded perspective view of a staple cartridge, staples, staple pushers and an actuation sled.

FIG. 3 illustrates a staple cartridge 40' including the staple drive assembly shown in FIG. 1. Staple cartridge 40' includes a plurality of fasteners or staples 50 and a corresponding number of staple pockets or retention slots 60. A tissue contacting surface 44 is defined by a top surface of staple cartridge 40'. A guide channel 42 extends substantially the length of staple cartridge 40' and is adapted for slidably receiving guide member 150 of actuation sled 110 as shown in FIG. 4. In FIG. 4, sled 110 is shown positioned at the proximal end of cartridge 40' with guide member 150 disposed in guide channel 42. Guide channel 42 cooperates with guide member 150 for aligning and positioning actuation sled 110 in staple cartridge 40' as it translates longitudinally from a proximal end to a distal end of staple cartridge 40'. Guide channel 42 may also facilitate passage of a knife blade (not shown) through cartridge 40', such as by mounting a knife blade to guide member 150.

In FIG. 5, a cross-sectional view taken along line 5-5 of FIG. 4, actuation sled 110 is shown disposed in the proximal end of staple cartridge 40' in a first or ready position. In the ready position, actuation sled 110 is capable of translating distally through staple cartridge 40' (i.e. in the direction indicated by arrow A) and sequentially engaging staple pushers 160 (FIG. 3) as discussed in detail hereinbelow. Actuation sled 110 is translatable along a longitudinal axis of staple cartridge 40' from its ready position to a second or end position located in a distal portion of staple cartridge 40'.

Figure 6:
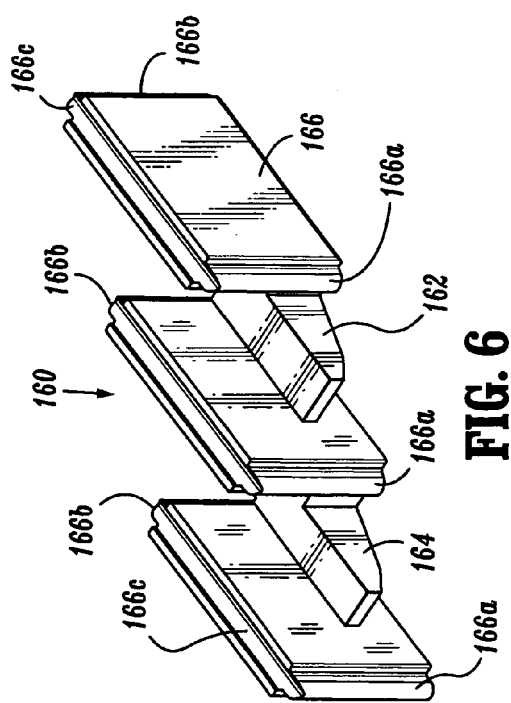
FIG. 6 is a front perspective view of the staple pusher of FIG. 1.
Figure 7:
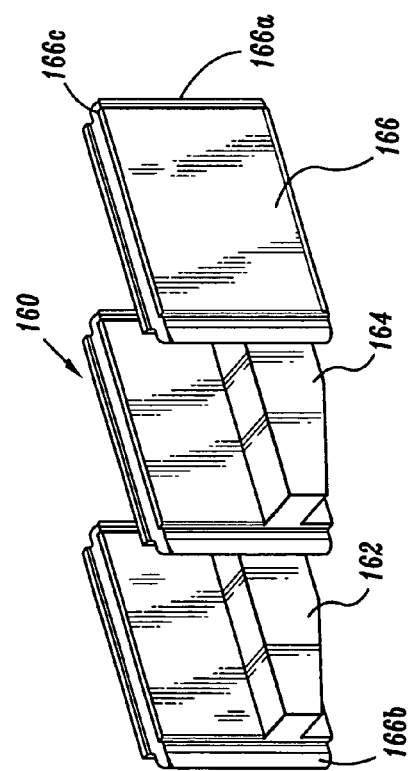
FIG. 7 is a rear perspective view of the staple pusher of FIG. 1.

Turning now to FIGS. 6-10, several views of one embodiment of staple pusher 160 are illustrated. Each staple pusher 160 includes a first cam member 162, a second cam member 164, and at least one prong or pusher plate 166. In one embodiment, each staple pusher 160 includes three pusher plates 166 that are laterally and longitudinally spaced apart from each other. Generally, first and second cam members 162, 164 and pusher plates 166 lie in a plane parallel to a longitudinal axis of staple cartridge 40'. As illustrated in FIGS. 6 and 7, each pusher plate 166 includes a leading edge 166a and a trailing edge 166b. In one embodiment, pusher plates 166 may be longitudinally spaced apart or staggered such that the longitudinal spacing between leading edges 166a of adjacent pusher plates 166 is about two-thirds the length of retention slot 60 or about two-thirds the length of an adjacent pusher plate 166. Further still, each pusher plate 166 includes a top surface 166c that is adapted for releasably engaging a backspan 52 of a staple 50 (see FIG. 1). Each retention slot 60 of staple cartridge 40' is configured for releasably receiving a staple 50 and a pusher plate 166 (see FIG. 3). Additionally, each staple includes two legs 54.

Figure 8:
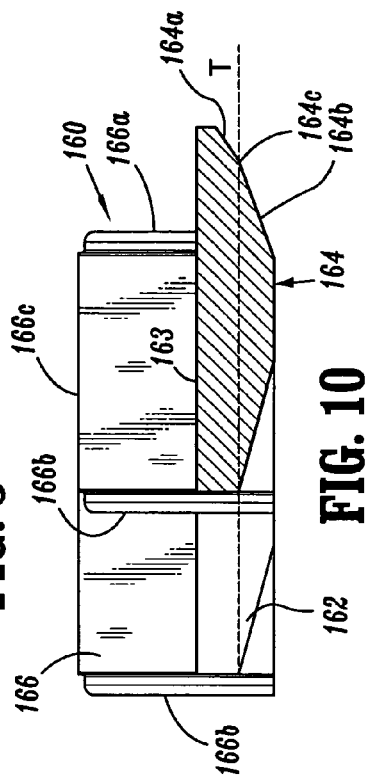
FIG. 8 is a top plan view of the staple pusher of FIG. 1.

As previously discussed, staple pusher 160 includes prongs or pusher plates 166 that are laterally and longitudinally spaced apart as well as first and second cam members 162, 164 interposed between adjacent pusher plates 166. More specifically, as discussed hereinabove, in one embodiment of the present disclosure, each staple pusher 160 includes a plurality of pusher plates 166 that are substantially parallel to a longitudinal axis of staple cartridge 40' and parallel to a centerline CL of each staple pusher 160 (FIG. 8). Additionally, first and second cam members 162, 164 are also substantially parallel to centerline CL (FIG. 8). Staple pusher 160, as viewed from left to right in FIG. 8 (i.e. distal to proximal), includes an inboard pusher plate 166 that is most distal along centerline CL. A middle pusher plate 166 is laterally spaced apart from inboard pusher plate 166 and is axially offset in the proximal direction from inboard pusher plate 166. An outboard pusher plate 166 is laterally spaced apart from middle pusher plate 166 and is axially offset in the proximal direction from middle pusher plate 166. Further still, first cam member 162 is disposed between inboard pusher plate 166 and middle pusher plate 166 while second cam member 164 is disposed between middle pusher plate 166 and outboard pusher plate 166. Configured thusly, staple pusher 160 has an arrangement where pusher plates 166 are longitudinally staggered from a distal portion of staple pusher 160 to a proximal portion of staple pusher 160 as seen in FIG. 8.

Figure 9:
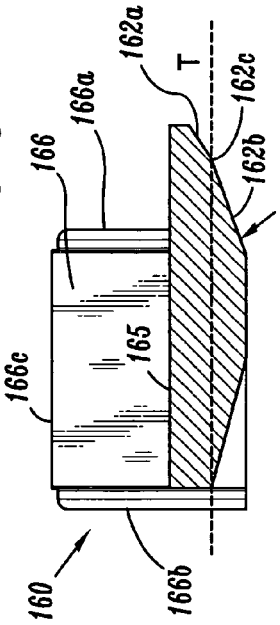
FIG. 9 is a side cross-sectional view taken along section line 9-9 of FIG. 8.
Figure 10:
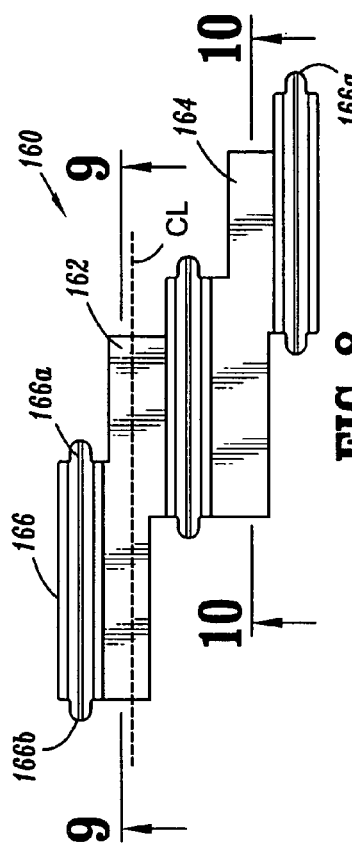
FIG. 10 is a side cross-sectional view taken along section line 10-10 of FIG. 8.

First and second cam members 162, 164 include respective first and second cam surfaces 162a, 162b and 164a, 164b (FIGS. 9 and 10). At the intersection of first and second cam surfaces 162a, 162b and 164a, 164b are respective transition points 162c, 164c. A plane T (FIG. 10) extending through transition points 162c, 164c is parallel to respective tops 163, 165 of cam members 162, 164. In one embodiment, first cam surfaces 162a, 164a define a first engagement or receiving angle with respect to tops 163, 165 of respective first and second cam members 162, 164. Second cam surfaces 162b, 164b define a second engagement or receiving angle with respect to plane T. First and second receiving angles are complementary to respective first and second drive angles of camming members 120, 140 of actuation sled 110 as discussed in detail hereinbelow. In one embodiment, the first receiving angles may be in a range of about 15° to about 55° while the second receiving angles may be in a range of about 5° to about 35°. In another embodiment, the first receiving angles may be in a range of about 25° to about 45° while the second receiving angles may be in a range of about 10° to about 30°. In a further embodiment, first receiving angles may be in a range of about 30° to about 40° while second receiving angles may be in a range of about 15° to about 25°.

Alternate embodiments of the presently disclosed staple pusher are illustrated in FIGS. 26-29 and discussed in detail hereinbelow. Initially referring to FIGS. 26-27, staple pusher 260 is illustrated and includes the same or substantially similar components to staple pusher 160. Each staple pusher 260 includes a first cam member 262, a second cam member 264, and a single prong or pusher plate 266. Generally, first and second cam members 262, 264 and pusher plates 266 lie in a plane parallel to a longitudinal axis of staple cartridge 40'. As illustrated in FIGS. 26 and 27, each pusher plate 266 includes a leading edge 266a and a trailing edge 266b. Further still, each pusher plate 266 includes a top surface 266c that is adapted for releasably engaging a backspan 52 of a staple 50 (see FIG. 1). Each retention slot 60 of staple cartridge 40' is configured for releasably receiving a staple 50 and a pusher plate 266 (see FIG. 3).

Staple pusher 260 includes a prong or a pusher plate 266 that separates first and second cam members 262, 264. More specifically, each staple pusher 260 includes a single pusher plate 266 that is substantially parallel to a longitudinal axis of staple cartridge 40' and parallel to a centerline CL of each staple pusher 260 (FIG. 27). Additionally, first and second cam members 262, 264 are also substantially parallel to centerline CL (FIG. 27).

First and second cam members 262, 264 include respective first and second cam surfaces 262a, 262b and 264a, 264b (FIG. 26). At the intersection of first and second cam surfaces 262a, 262b and 264a, 264b are respective transition points 262c, 264c. A plane T (FIG. 26) extending through transition points 262c, 264c is parallel to respective tops 263, 265. In one embodiment, first cam surfaces 262a, 264a define a first engagement or receiving angle with respect to tops 263, 265 of respective first and second cam members 262, 264. Second cam surfaces 262b, 264b define a second engagement or receiving angle with respect to plane T. First and second receiving angles are complementary to respective first and second drive angles of camming members 120, 140 as discussed in detail hereinbelow. In one embodiment, the first receiving angles may be in a range of about 15° to about 55° while the second receiving angles may be in a range of about 5° to about 35°. In another embodiment, the first receiving angles may be in a range of about 25° to about 45° while the second receiving angles may be in a range of about 10° to about 30°. In a further embodiment, first receiving angles may be in a range of about 30° to about 40° while second receiving angles may be in a range of about 15° to about 25°.

Referring now to FIGS. 28 and 29, another embodiment of the staple pusher of the present disclosure is shown and referenced as 360. Each staple pusher 360 includes a first cam member 362, a second cam member 364, and two prongs or pusher plates 366 that are laterally and longitudinally spaced apart from each other. Generally, first and second cam members 362, 364 and pusher plates 366 lie in a plane parallel to a longitudinal axis of staple cartridge 40'. As illustrated in FIGS. 28 and 29, each pusher plate 366 includes a leading edge 366a and a trailing edge 366b. Pusher plates 366 may be longitudinally spaced apart or staggered such that the longitudinal spacing between leading edges 366a of adjacent pusher plates 366 is about two-thirds the length of retention slot 60 or about two-thirds the length of pusher plate 366. Further still, each pusher plate 366 includes a top surface 366c that is adapted for releasably engaging a backspan 52 of a staple 50 (see FIG. 1). Each retention slot 60 of staple cartridge 40' is configured for releasably receiving a staple 50 and a pusher plate 366 (see FIG. 3).

First and second cam members 362, 364 include respective first and second cam surfaces 362a, 362b and 364a, 364b (FIGS. 28 and 29). At the intersection of first and second cam surfaces 362a, 362b and 364a, 364b are respective transition points 362c, 364c. A plane T (FIG. 28) extending through transition points 362c, 364c is parallel to respective tops 363, 365. In one embodiment, first cam surfaces 362a, 364a define a first engagement or receiving angle with respect to tops 363, 365 of respective first and second cam members 362, 364. Second cam surfaces 362b, 364b define a second engagement or receiving angle with respect to plane T. First and second receiving angles are complementary to respective first and second drive angles of camming members 120, 140 as discussed in detail hereinbelow. In one embodiment, the first receiving angles may be in a range of about 15° to about 55° while the second receiving angles may be in a range of about 5° to about 35°. In another embodiment, the first receiving angles may be in a range of about 25° to about 45° while the second receiving angles may be in a range of about 10° to about 30°. In a further embodiment, first receiving angles may be in a range of about 30° to about 40° while second receiving angles may be in a range of about 15° to about 25°.

With reference to FIGS. 11-15, several views of one embodiment of actuation sled 110 are shown. First and second camming members 120, 140 each include a first or leading cam wedge 122, 142, respectively, that is laterally and longitudinally spaced apart from a second or trailing cam wedge 124, 144, respectively. The lateral and longitudinal offset distances of each pair of camming wedges substantially corresponds to the lateral and longitudinal offset distances between corresponding cam members 162, 164. First cam wedges 122, 142 are laterally and longitudinally spaced from second cam wedges 124, 144, respectively, by a substantially identical amount such that first and second camming members 120, 140 are symmetrical about a central longitudinal axis of actuation sled 110. Leading cam wedges 122, 142 include respective first and second drive faces 122a, 122b, 142a, and 142b. First drive faces 122a, 142a form first drive angles on camming members 120, 140 with respect to base 112 of actuation sled 110. At the intersection of first and second drive faces 122a, 142a and 122b, 142b are respective transition points 123, 143. A plane X extending through transition points 123, 143 is substantially parallel to base 112. Second drive faces 122b, 142b form respective second drive angles on camming members 120, 140 with respect to plane X. Plane X is also substantially parallel to tissue contacting surface 44 of staple cartridge 40'.

Similarly, trailing cam wedges 124, 144 include respective first and second drive faces 124a, 124b, 144a, and 144b. First drive faces 124a, 144a form first drive angles on camming members 120, 140 with respect to base 112 (FIG. 5) of actuation sled 110. At the intersection of first and second drive faces 124a, 124b and 144a, 144b are respective transition points 125, 145. Plane X extends through transition points 125, 145 and is substantially parallel to base 112. Second drive faces 124b, 144b form respective second drive angles on camming members 120, 140 with respect to plane X. In one embodiment, first drive angles may be in a range of about 15° to about 55° while second drive angles may be in a range of about 5° to about 35°. In another embodiment, first drive angles may be in a range of about 25° to about 45° while second drive angles may be in a range of about 10° to about 30°. In a further embodiment, first drive angles may be in a range of about 30° to about 40° while second drive angles may be in a range of about 15° to about 25°.

Figure 18:
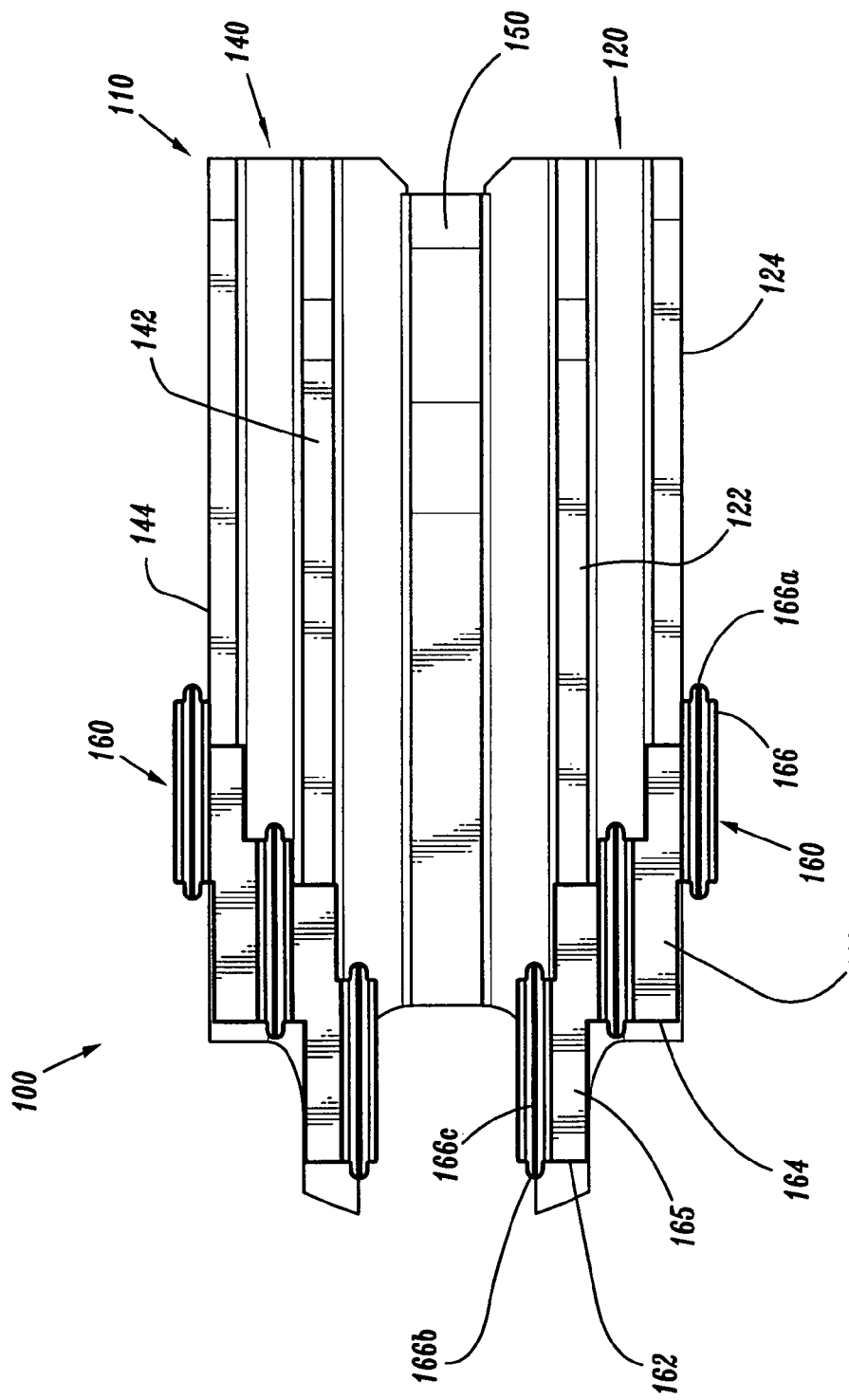
FIG. 18 is a top plan view taken along section line 18-18 of the staple drive assembly of FIG. 17.

Interaction between actuation sled 110 and staple pusher 160 of staple drive assembly 100 is shown in FIGS. 16-18 and discussed in detail hereinafter. Initially, as illustrated in FIG. 16, actuation sled 110 translates distally through staple cartridge 40' in the direction indicated by arrow A (see also FIG. 5) causing first drive face 122a to slidably engage first cam surface 162a and urge staple pusher 160 from its first or rest position in a generally vertical direction as indicated by arrow B. Because the lateral and longitudinal offset distances of wedges 122, 124 correspond to the lateral and longitudinal offset distances between cam wedges 162, 164, first drive face 124a substantially simultaneously slidably engages first cam surface 164a thereby urging staple pusher 160 in a generally vertical direction as indicated by arrow B. Since cam surfaces 162a and 164a are longitudinally offset, staple pusher 160 is driven in a controlled and balanced manner and any tendency of staple pusher 160 to tilt or rotate counterclockwise (as viewed in FIGS. 16-17) is minimized as staple pusher 160 is driven through retainer slot 60. First drive faces 122a, 124a and respective first cam surfaces 162a, 164a have complementary angles that maximize translation of longitudinal motion of actuation sled 110 to vertical motion of staple pusher 160.

Referring now to FIG. 17, continued distal movement of actuation sled 110 further urges staple pusher 160 generally vertically to an intermediate position, such that second drive faces 122b, 124b slidably engage respective second cam surfaces 162b, 164b while first drive faces 122a, 124a substantially simultaneously disengage from respective first cam surfaces 162a, 164a. Similarly, second drive faces 122b, 124b and respective second cam surfaces 162b, 164b have complementary angles to maximize translation of longitudinal motion of actuation sled 110 to vertical motion of staple pusher 160. The corresponding lateral and longitudinal offset of second drive faces 122b, 124b and respective second cam surfaces 162b, 164b continue to control the advancement of staple pusher 160 so as to minimize any tendency of staple pusher 160 to tilt or rotate in a counterclockwise direction as viewed in FIGS. 16-17. Continuing distal movement of actuation sled 110 continues to urge staple pusher 160 vertically to its second or end position immediately prior to the disengagement between second drive faces 122b, 124b and respective second cam surfaces 162b, 164b.

Since the interaction between second camming member 140 and staple pusher 160 is substantially identical to the intersection of first camming member 120 and pusher 160, the intersection of second camming member 140 and staple pusher 160 will not be described in detail herein.

Longitudinal motion of actuation sled 110 in the direction indicated by arrow A results in first and second camming members 120, 140 slidably engaging staple pushers 160 as shown in FIGS. 16-18. Sliding engagement between leading cam wedges 122, 142 and first cam members 162 in cooperation with the substantially simultaneous engagement between trailing cam wedges 124, 144 and second cam members 164 improve the longitudinal stability of the staple pushers 160 during vertical motion as follows. Leading cam wedges 122, 142 are longitudinally spaced apart from trailing cam wedges 124, 144 by a predetermined amount. Since respective first and second cam members 162, 164 are longitudinally spaced apart by a comparable, but complementary amount, longitudinal movement of actuation sled 110 results in the substantially simultaneous, but offset engagement of leading cam wedges 122, 124 and trailing cam wedges 124, 144 with respective first and second cam members 162, 164 thereby transferring the longitudinal movement of actuation sled 110 to vertical movement of staple pusher 160 at longitudinally spaced apart impact points. By transferring longitudinal movement of actuation sled 110 to each staple pusher 160 at two longitudinally spaced apart impact points, substantially balanced vertical movement of each staple pusher 160 is achieved. Since there is two point contact between first and second camming members 120, 140 and respective first and second cam members 162, 164 throughout the vertical travel of each staple pusher 160, pivoting or tilting of each staple pusher 160 is minimized due to the two-point contact arrangement. Minimizing pivoting or tilting of each staple pusher 160 during vertical travel further minimizes pivoting or tilting of each staple 50 as each staple 50 is driven vertically in its respective retention slot 60. This provides more precise contact of a staple with an anvil pocket (not shown) and thus, improved staple formation.

In addition, the lateral offset between cam wedges 122, 124 of first camming member 120 and cam wedges 142, 144 of second camming member 140 inhibits "rocking" of staple pusher 160. "Rocking" of staple pushers may occur when the lifting force applied to the staple pusher by the actuation sled is not balanced creating a tendency for the staple pusher to "rock" in a direction that is transverse to the movement of the actuation sled. This "rocking" movement may cause misalignment of the staple during a firing sequence resulting in non-uniform staple formation. In extreme circumstances, "rocking" may cause a "front jump" staple formation wherein the rear leg of a staple exits the staple cartridge at an angle and enters the anvil pocket at the same location as the front leg of the same staple. By providing actuation sled 110 with laterally offset cam wedges, actuation sled 110 contacts staple pusher 160 at two laterally spaced contact points substantially simultaneously, thereby imparting a lifting force to staple pusher 160 that is substantially balanced between first and second cam members 162, 164. Therefore, engagement of actuation sled 110 with staple pusher 160 results in substantially even vertical motion of staple pusher 160 and inhibits "rocking" of staple pusher 160 and inhibits front jump staple formation.

Further still, as previously discussed, each cam wedge (122, 124, 142, 144) defines a plurality of receiving angles that are complementary to drive angles defined by cam members 162, 164. When the first drive angle is greater than the second drive angle, single point contact between the staple pusher and the cam wedge may occur. Instability of the staple pusher due to such single point contact can also result in tilting or rotation of the staple pusher during firing. Such instability is most likely to occur as the staple pusher transitions from contacting one drive surface to the other drive surface. As described above, unbalanced vertical movement of staple pusher 160 can cause staple pusher 160 to travel vertically at an angle such that top surfaces 166c (FIG. 1) of staple pusher 160 are not substantially parallel to tissue contacting surface 44 or backspan 52 of staple 50 (FIG. 3). This may lead to improperly formed staples, misalignment of the staples with the anvil pockets, or misalignment of the staples with the retention slots. By providing different angles on each cam wedge, an angular differential is defined wherein the angular differential minimized "rotation" of staple pusher 160.

Interaction between actuation sled 110 and staple pushers 260, 360 is substantially similar to the interaction described hereinabove between actuation sled 110 and staple pusher 160 and will not be discussed in detail. It is sufficient to note that staple pushers 260, 360 may be freely substituted for staple pusher 160.

Referring now to FIGS. 19-25, another embodiment of the presently disclosed staple drive assembly 200 is illustrated (FIGS. 24-25). Staple drive assembly 200 includes an actuation sled 210 (FIGS. 19-23) and at least one staple pusher 160 (FIGS. 6-10). Actuation sled 210 is adapted and configured for use in staple cartridge 40' as an alternative for actuation sled 110. As seen in FIGS. 19-23, actuation sled 210 includes a first camming member 220, a second camming member 240, and a guide member 250. First and second camming members 220, 240 include respective first or leading cam wedges 222, 242 and respective second or trailing cam wedges 224, 244.

Similar to actuation sled 110, leading cam wedges 222, 242 of actuation sled 210 include first drive faces 222a, 242a and second drive faces 222b, 242b. Interposed between first drive faces 222a, 242a and second drive faces 222b, 242b are respective first and second transition points 223, 243. First drive faces 222a, 242a extend proximally from a distal point 214 both longitudinally and vertically thereby forming a first drive angle with respect to base 212. Trailing cam wedges 224, 244 are longitudinally spaced apart from leading cam wedges 222, 242 by a predetermined distance. First drive faces 224a, 244a of trailing cam wedges 224, 244 extend both longitudinally and vertically in a proximal direction from respective origin points 214a, 214b to form the first drive angle with respect to base 212. A plane X' extending through transition points 223, 243 (FIG. 23) of leading cam wedges 222, 242 is parallel to base 212. Second drive faces 222b, 242b form respective second drive angles with respect to plane X'. Additionally, plane X' extends through transition points 225, 245 (FIG. 23) of trailing cam wedges 224, 244 and is substantially parallel to base 212. Plane X' is also substantially parallel to tissue contacting surface 44 of staple cartridge 40'. Second drive faces 224b, 244b form respective second drive angles with respect to plane X'. In one embodiment, first drive angles may be in a range of about 5° to about 35° while second drive angles may be in a range of about 20° to about 55°. In another embodiment, first drive angles may be in a range of about 10° to about 30° while second drive angles may be in a range of about 25° to about 45°. In a further embodiment, first drive angles may be in a range of about 15° to about 25° while the second drive angles may be in a range of about 30° to about 40°. By providing actuation sled 210 with first drive faces 222a, 242a having a flatter initial engaging surface having a lower angle relative to a plane parallel to base 212, interaction between actuation sled 210 and each staple pusher 160 is more controllable. As actuation sled 210 translates through staple cartridge 40' and interacts with each staple pusher as discussed above, actuation sled 210 gradually and controllably urges each staple pusher 160 vertically as actuation sled 210 translates through staple cartridge 40'.

In staple drive assembly 200, the interaction between actuation sled 210 and staple pusher 160 is illustrated in FIGS. 24-25 and discussed in detail hereinafter. As actuation sled 210 moves distally through staple cartridge 40' (see FIG. 5) in a generally horizontal direction as indicated by arrow A, first drive faces 222a, 224a contact respective second cam surfaces 162b, 164b and urge staple pusher 160 in a generally vertical direction as indicated by arrow B from its first or rest position. Since the first drive angle is defined by first drive faces 222a, 224a and is complementary to the second receiving angle defined by second cam surfaces 162b, 164b, horizontal movement of actuation sled 210 in direction A causes vertical movement of staple pusher 160 in direction B.

As actuation sled 210 continues to move in the direction of arrow A, second drive faces 222b, 224b engage respective first cam surfaces 162a, 164a and first drive faces 222a, 224a remain engaged with their respective second cam surfaces 162b, 164b, thereby providing additionally longitudinal and vertical stability of staple pusher 160. After actuation sled 210 moves a predetermined distance in the direction of arrow A, first drive faces 222a, 224a disengage from their respective second cam surfaces 162b, 164b while second drive faces 222b, 224b remain engaged with their respective first cam surfaces 162a, 164a. The second drive angle defined by second drive faces 222b, 224b is complementary to the first receiving angle defined by first cam surfaces 162a, 164a further urging staple pusher 160 in the direction of arrow B through an intermediate position. Continuing distal movement of actuation sled 210 continues to urge staple pusher 160 vertically to its second or end position immediately prior to the disengagement between second drive faces 222b, 224b and respective second cam surfaces 162a, 164a. A cam wedge having a first drive angle which is less than the second drive angle creates multiple contact points between the cam wedge and the staple pusher as the staple pusher transitions from contacting the first drive surface to contacting the second drive surface, thereby further enhancing the stability of the staple pusher during firing. In addition, providing a first drive angle less than the second drive angle minimizes misalignment since there is additional support for the staple pusher during its vertical movement.

Since the interaction between second camming member 240 and staple pusher 160 is substantially identical to the interaction between first camming member 220 and staple pusher 160, the interaction between second camming member 240 and staple pusher 160 will not be described in further detail herein. It is sufficient to note that staple pushers 260, 360 may be freely substituted for staple pusher 160.

The sliding engagement between leading cam wedges 222, 242 and first cam members 162 in cooperation with the substantially simultaneous engagement between trailing cam wedges 224, 244 and second cam members 164 is substantially similar to that discussed hereinabove for staple drive assembly 100 and improves the longitudinal stability of the staple pushers 160 during vertical motion.

Interaction between actuation sled 210 and staple pushers 260, 360 is substantially similar to the interaction described hereinabove between actuation sled 210 and staple pusher 160 and will not be discussed in detail.

Referring now to FIGS. 30-36, another embodiment of the presently disclosed staple drive assembly 300 is illustrated (FIGS. 35-36). Staple drive assembly 300 includes an actuation sled 310 (FIGS. 30-34) and at least one staple pusher 160 (FIGS. 6-10). Actuation sled 310 is adapted and configured for use in staple cartridge 40' as an alternative for actuation sled 110 or actuation sled 210.

As shown in FIGS. 30-34, actuation sled 310 includes a first camming member 320, a second camming member 340, and a guide member 350. First and second camming members 320, 340 include respective first or leading cam wedges 322, 342 and respective second or trailing cam wedges 324, 344.

Similar to actuation sleds 110 and 210, trailing cam wedges 324, 344 are laterally and longitudinally spaced apart from leading cam wedges 322, 342 by a predetermined distance. Leading cam wedges 322, 342 include leading drive faces 322a, 342a while trailing cam wedges 324, 344 include trailing drive faces 324a, 344a. Drive faces 324a, 344a of trailing cam wedges 324, 344 extend both longitudinally and vertically in a proximal direction from respective origin points 314a, 314b. Drive faces 322a, 342a of leading cam wedges also extend both longitudinally and vertically in a proximal direction from respective origin points 316a, 316b. Drive faces 322a, 342a, 324a, 344a each form a drive angle with respect to base 312 wherein the drive angle is substantially identical for drive faces 322a, 342a, 324a, 344a. In one embodiment, the drive angle may be in a range of about 15° to about 25°. In another embodiment, the drive angle may be in a range of about 10° to about 30°. In a further embodiment, the drive angle may be in a range of about 5° to about 35°.

In staple drive assembly 300, the interaction between actuation sled 310 and staple pusher 160 is illustrated in FIGS. 35-36 and discussed in detail hereinafter. As actuation sled 310 moves distally through staple cartridge 40' (see FIG. 5) in a generally horizontal direction as indicated by arrow A, drive faces 322a, 324a engage cam surfaces 162, 164 of staple pusher 160 and urge staple pusher 160 in a generally vertical direction as indicated by arrow B from its first or rest position. As in previous embodiments, cam surfaces 162, 164 define receiving angles that are complementary to the drive angle formed by drive faces 322a, 324a. Cam surfaces 162, 164 are laterally and longitudinally spaced apart so that the spacing of cam surfaces 162, 164 corresponds to the lateral and longitudinal spaced of the cam wedge drive faces. As actuation sled 310 moves distally through staple cartridge 40', cam surfaces 162, 164 of staple pusher 160 maintain their engagement with drive faces 322a, 324a of actuation sled 310. As will be appreciated, the lateral and longitudinal spacing of the cam wedges and cam surfaces provides improved stability to the staple pusher during firing, as described above, albeit without the varied drive angles of the drive surfaces.

Since the interaction between second camming member 340 and staple pusher 160 is substantially identical to the interaction between first camming member 320 and staple pusher 160, the interaction between second camming member 340 and staple pusher 160 will not be described in further detail herein. It is sufficient to note that staple pushers 260, 360 may be freely substituted for staple pusher 160.

The sliding engagement between leading cam wedges 322, 342 and first cam members 162 in cooperation with the substantially simultaneous engagement between trailing cam wedges 324, 344 and second cam members 164 is substantially similar to that discussed hereinabove for staple drive assembly 100, 200 and improves the longitudinal stability of the staple pushers 160 during vertical motion.

Interaction between actuation sled 310 and staple pushers 260, 360 is substantially similar to the interaction described hereinabove between actuation sled 310 and staple pusher 160 and will not be discussed in detail.

Referring now to FIGS. 37-44 another embodiment of the presently disclosed staple drive assembly 400 is illustrated (FIGS. 43-44). Staple drive assembly 400 includes an actuation sled 410 (FIGS. 37-41) and at least one staple pusher 460 (FIGS. 42A-42B). Actuation sled 410 is adapted and configured for use in staple cartridge 40' (FIG. 4).

As shown in FIGS. 42A-B, staple pusher 460 includes a first cam member 462, a second cam member 464, and at least one prong or pusher plate 466. In one embodiment, staple pusher 460 includes three pusher plates 466 that are laterally spaced apart from each other by first and second cam members 462, 464. Generally, first and second cam members 462, 464 and pusher plates 466 lie in a plane parallel to the longitudinal axis of staple cartridge 40'. Each pusher plate 466 includes a leading edge 466a, a trailing edge 466b, and a top surface 466c. In one embodiment, one pusher plate 466 may be longitudinally spaced such that pusher plates 466 are in a staggered orientation with respect to each other such that the two outside pusher plates are laterally aligned with each other, but the middle pusher plate is displaced from lateral alignment with the side pusher plates. An example of a suitable staple pusher is disclosed in U.S. Pat. No. 4,978,049 to Green, currently owned by Tyco Healthcare Group LP, the entire contents of which are incorporated herein by reference.

First and second cam members 462, 464 include respective cam surfaces 462aa, 464a (FIG. 42A). In one embodiment, cam surfaces 462a, 464a define an engagement or receiving angle with respect to tops 463, 465 of respective first and second cam members 462, 464. The receiving angle is complementary to a first drive angle of camming members 420, 440 of actuation sled 410 as discussed in detail hereinbelow. In one embodiment, the receiving angle may be in a range of about 15° to about 25°. In another embodiment, the receiving angle may be in a range of about 17° to about 23°. In a further embodiment, the receiving angle may be in a range of about 19° to about 21°.

With reference to FIGS. 37-41, actuation sled 410 of staple drive assembly 400 includes first and second camming members 420, 440 each having a first cam wedge 422, 442, respectively, that is laterally spaced apart from a second cam wedge 424, 444, respectively. First cam wedges 422, 442 are laterally spaced from second cam wedges 424, 444, respectively, by a substantially identical amount such that first and second camming members 420, 440 are substantially symmetrical about a central longitudinal axis of actuation sled 410. Each cam wedge 422, 424, 442, 444 includes a plurality of drive faces as shown in FIGS. 37-38 where each of the respective drive faces are indicated by reference characters "a-d." A plane Y extends through the intersection between drive faces "a" and "b." Plane Y is substantially parallel to a base 412 and to tissue contacting surface 44 of staple cartridge 40' (see FIG. 3). First cam wedge 422 will be discussed in detail below to illustrate the relationship between the drive faces with cam wedges 424, 442, and 444 having substantially identical relationships.

First cam wedge 422 of cam member 420 includes first through fourth drive faces 422a, 422b, 422c, and 422d as shown in FIG. 41. First drive face 422a defines a first angle with respect to base 412 while second drive face 422b defines a second drive angle with respect to plane Y. In addition, the slope of drive faces 422c and 422d are substantially identical to the slopes of drive faces 422a and 422b respectively. In one embodiment of actuation sled 410, the first and third drive angles (i.e. defined by drive faces 422a, 442c) may be in a range of about 15° to about 25°. In another embodiment, the first and third drive angles may be in a range of about 17° to about 23°. In a further embodiment, the first and third drive angles may be in a range of about 19° to about 21°. The second drive angle (i.e. defined by drive faces 422b, 422d) may be in a range of about 26° to 36°. In another embodiment, the second drive angle may be in a range of about 28° to 34°. In a further embodiment, the second drive angle may be in a range of about 30° to about 32°.

Interaction between actuation sled 410 and staple pusher 460 of staple drive assembly 400 is shown in FIGS. 43-44 and discussed in detail hereinafter. Initially, as illustrated in FIG. 43, actuation sled 410 translates distally through staple cartridge 40' in the direction indicated by arrow A causing cam wedges 422, 424 of first cam member 420 to slidably engage staple pusher 460. Specifically, first drive faces 422a, 424a substantially simultaneously slidably engage respective cam surfaces 462a, 464a and urge staple pusher 460 from its first or rest position in a generally vertical direction as indicated by arrow B. In one embodiment of staple drive assembly 400, the first and third drive angles of cam wedges 422, 424, 442, and 444 are complementary to the first receiving angle of cam surfaces 462a, 464a. As actuation sled 410 moves distally with drive faces 422a, 424a in slidable engagement with respective cam surfaces 462a, 464a (i.e. engaging the first drive angle), top surfaces 466c of pusher plates 466 engage backspan 52 of staple 50 and urge staple 50 in a substantially vertical direction and engages tissue in contact with tissue contacting surface 44. As actuation sled 410 continues distal movement, cam surfaces 462a, 464a slidably engage respective second drive faces 422b, 424b continuing to urge staple 50 vertically. As illustrated in FIG. 44, continued distal translation of actuation sled 410 causes cam surfaces 462a, 464a to slidably engage drive faces 422c, 424c (i.e. engaging the third drive angle), thereby moving legs 54 of staple 50 into engagement with anvil assembly 70 to form completed staples 50. By providing first and third drive angles of respective first drive faces 422a, 424a, and third drive faces 422c, 424c that are complementary to the receiving angles of cam surfaces 462a, 464a, the interaction between the distal movement of actuation sled 410 and staple pusher 460 may reduce the firing force necessary to fire staples 50. In addition to matching the drive angles and the receiving angles, first drive faces 422a, 424a are spaced apart from third drive faces 422c, 424c by a predetermined distance thereby further minimizing kicking of staple pusher 460 as staple 50 engages tissue and anvil assembly 70, respectively.

Since the interaction between second camming member 440 and staple pusher 460 is substantially identical to the interaction of first camming member 420 and pusher 460, the interaction of second camming member 440 and staple pusher 460 will not be described in detail herein.

In addition, another embodiment of the staple drive assembly is illustrated in FIGS. 45-51 and referenced generally as 500 (FIGS. 50-51). Staple drive assembly 500 includes actuation sled 510 (FIGS. 45-49) having first and second camming members 520, 540 each having a first cam wedge 522, 542, respectively, that is laterally spaced apart from a second cam wedge 524, 544, respectively. First cam wedges 522, 542 are laterally spaced from second cam wedges 524, 544, respectively, by a substantially identical amount such that first and second camming members 520, 540 are substantially symmetrical about a central longitudinal axis of actuation sled 510. Each cam wedge 522, 524, 542, 544 includes a plurality of drive faces as shown in FIGS. 45-46 where each of the respective drive faces are indicated by reference characters "a-d." A plane Y extends through the intersection between drive faces "a" and "b." Plane Y is substantially parallel to a base 512 and to tissue contacting surface 44 of staple cartridge 40' (FIG. 3). In addition, first cam wedges 522, 542 are longitudinally spaced from second cam wedges 524, 544. First cam wedge 522 will be discussed in detail below to illustrate the relationship between the drive faces with cam wedges 524, 542, and 544 having substantially identical relationships.

First cam wedge 522 of cam member 520 includes first through fourth drive faces 522a, 522b, 522c, and 522d as shown in FIG. 49. First drive face 522a defines a first angle with respect to base 512 while second drive face 522b defines a second drive angle with respect to plane Y. In addition, the slope of drive faces 522c and 522d are substantially identical to the slopes of drive faces 522a and 522b respectively. In one embodiment of actuation sled 510, the first and third drive angles (i.e. defined by drive faces 522a, 542c) may be in a range of about 15° to about 55°. In another embodiment, the first and third drive angles may be in a range of about 25° to about 45°. In a further embodiment, the first and third drive angles may be in a range of about 30° to about 40°. The second drive angle (i.e. defined by drive faces 522b, 522d) may be in a range of about 5° to 35°. In another embodiment, the second drive angle may be in a range of about 10° to 30°. In a further embodiment, the second drive angle may be in a range of about 15° to about 25°.

Interaction between actuation sled 510 and staple pusher 160 (FIG. 6) of staple drive assembly 500 is shown in FIGS. 50-51 and discussed in detail hereinafter. Initially, as illustrated in FIG. 50, actuation sled 510 translates distally through staple cartridge 40' in the direction indicated by arrow A causing first drive face 522a to slidably engage first cam surface 162a and urge staple pusher 160 from its first or rest position in a generally vertical direction as indicated by arrow B. Substantially simultaneously, first drive face 524a slidably engages first cam surface 164a thereby urging staple pusher 160 in a generally vertical direction as indicated by arrow B. Since cam surfaces 162a, 164a and first drive faces 522a, 524a are longitudinally offset, staple pusher 160 is driven in a balanced manner to minimize tipping or tilting of staple pusher 160 as it is driven through retainer slot 60. First drive faces 522a, 524a and respective first cam surfaces 162a, 164a have complementary angles that maximize translation of longitudinal motion of actuation sled 510 to vertical motion of staple pusher 160.

Referring now to FIG. 51, continued distal movement of actuation sled 510 further urges staple pusher 160 generally vertically to an intermediate position, such that second drive faces 522b, 524b slidably engage respective second cam surfaces 162b, 164b while first drive faces 522a, 524a substantially simultaneously disengage from respective first cam surfaces 162a, 164a. Similarly, second drive faces 522b, 524b and respective second cam surfaces 162b, 164b have complementary angles to maximize translation of longitudinal motion of actuation sled 510 to vertical motion of staple pusher 160. Continuing distal movement of actuation sled 510 continues to urge staple pusher 160 vertically to its second or end position immediately prior to the disengagement between second drive faces 522b, 524b and respective second cam surfaces 162b, 164b.

Since the interaction between second camming member 540 and staple pusher 160 is substantially identical to the intersection of first camming member 520 and pusher 160, the intersection of second camming member 540 and staple pusher 160 will not be described in detail herein.

Longitudinal motion of actuation sled 510 in the direction indicated by arrow A results in first and second camming members 520, 540 slidably engaging staple pushers 160 as shown in FIGS. 50-51. Sliding engagement between leading cam wedges 522, 542 and second cam members 164 in cooperation with the substantially simultaneous engagement between trailing cam wedges 524, 544 and first cam members 162 improve the longitudinal stability of the staple pushers 160 during vertical motion as follows. Leading cam wedges 522, 542 are longitudinally spaced apart from trailing cam wedges 524, 544 by a predetermined amount. Since respective first and second cam members 162, 164 are longitudinally spaced apart by a comparable, but complementary amount, longitudinal movement of actuation sled 510 results in the substantially simultaneous engagement of leading cam wedges 522, 524 and trailing cam wedges 524, 544 with respective first and second cam members 162, 164 thereby transferring the longitudinal movement of actuation sled 510 to vertical movement of staple pusher 160 at longitudinally spaced apart impact points. By transferring longitudinal movement of actuation sled 510 to each staple pusher 160 at two longitudinally spaced apart impact points, substantially balanced vertical movement of each staple pusher 160 is achieved. Since there is two point contact between first and second camming members 520, 540 and respective first and second cam members 162, 164 throughout the vertical travel of each staple pusher 160, pivoting or tilting of each staple pusher 160 is minimized due to the two-point contact arrangement. Minimizing pivoting or tilting of each staple pusher 160 during vertical travel further minimizes pivoting or tilting of each staple 50 as each staple 50 is driven vertically in its respective retention slot 60. This provides more precise contact of a staple with an anvil pocket (not shown) and thus, improved staple formation.

Interaction between actuation sled 510 and staple pushers 260, 360 is substantially similar to the interaction described hereinabove between actuation sled 510 and staple pusher 160 and will not be discussed in detail. It is sufficient to note that staple pushers 260, 360 may be freely substituted for staple pusher 160.

Figure 52:
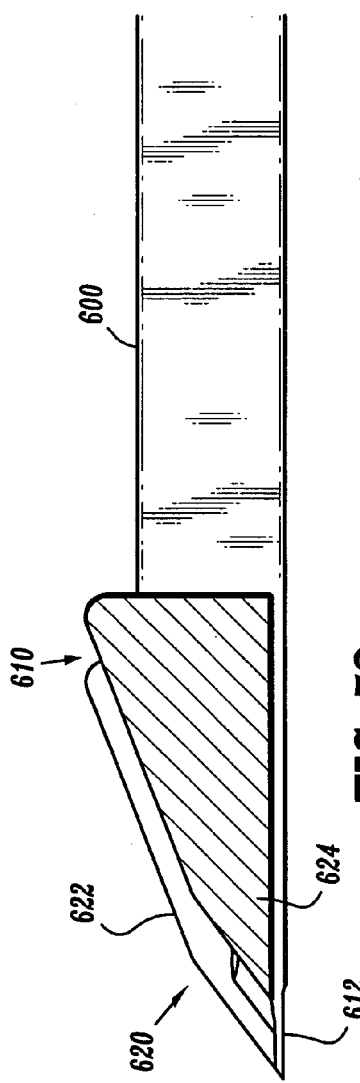
FIG. 52 is a side cross-sectional view of an end portion of an actuation member according to an embodiment of the present disclosure.

Further embodiments of the present disclosure are illustrated in FIGS. 52-56 and discussed in detail hereinafter. The embodiments that are illustrated in FIGS. 52-56 include a cam member or actuation bar. An example of a suitable cam bar and associated apparatus is disclosed in U.S. Pat. No. 6,619,529 to Green et al., currently owned by Tyco Healthcare Group LP, the contents of which are hereby incorporated by reference in their entirety. In addition, the staple cartridge 40' (FIG. 3) may include longitudinal slots as disclosed in the '529 for providing lateral stability to the cam bars as they translate longitudinally through staple cartridge 40'. Referring initially to FIG. 52, a portion of a cam bar or actuation member 600 is illustrated. Actuation member 600 includes a distal end 610 wherein distal end 610 includes the same or substantially similar components as included in actuation sled 110 (FIG. 11). Distal end 610 includes a base 612, a first camming member 620, and a second camming member 640 (not shown). First and second camming members 620, 640 include respective first or leading cam wedges 622, 642 and respective second or trailing cam wedges 624, 644. The configuration and relationships between the components of distal end 610 are substantially similar to those components of actuation sled 110 and will not be described in detail herein. Essentially, distal end 610 includes actuation sled 110 using reference characters 6xx in lieu of 1xx used in describing actuation sled 110. In addition, actuation member 600 and distal end 610 may be substituted for actuation sled 110 in staple cartridge 40' (FIG. 4). The interaction of distal end 610 and staple pusher 160 (FIG. 6) is substantially similar to the interaction of actuation sled 110 and staple pusher 160 (see FIGS. 16-17) and will not be discussed in detail herein. Further still, distal end 610 is adapted to cooperate with staple pusher 260 (FIG. 26) or staple pusher 360 (FIG. 28). As shown, cam wedges 622, 642 are laterally and longitudinally offset and engage corresponding surfaces on the staple pusher (not shown) for improving the stability of the staple pusher during firing, as described above with respect to cam wedges 122, 142.

Figure 53:
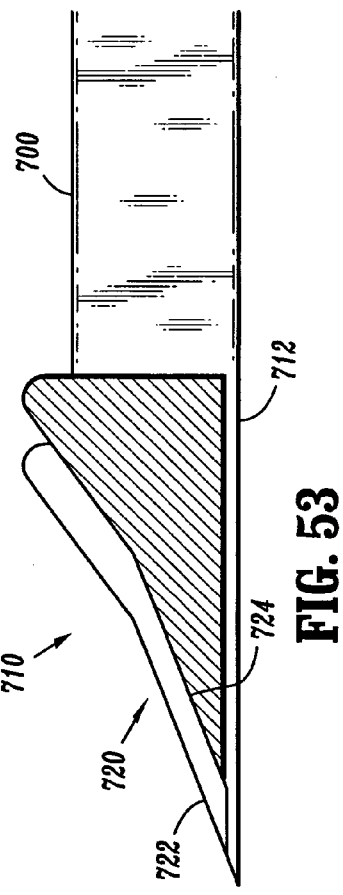
FIG. 53 is a side cross-sectional view of an end portion of an actuation member according to an alternate embodiment of the present disclosure.

In FIG. 53, a portion of an actuation member 700 is shown and includes a distal end 710 having the same or substantially similar components as included in actuation sled 210 (FIG. 19). Distal end 710 includes a base 712, a first camming member 720, and a second camming member 740 (not shown). First and second camming members 720, 740 include respective first or leading cam wedges 722, 742 and respective second or trailing cam wedges 724, 744. The configuration and relationships between the components of distal end 710 are substantially similar to those components of actuation sled 210 and will not be described in detail herein. Essentially, distal end 710 includes actuation sled 210 using reference characters 7xx in lieu of 2xx used in describing actuation sled 210. In addition, actuation member 700 and distal end 710 may be substituted for actuation sled 210 in staple cartridge 40'. The interaction of distal end 710 and staple pusher 160 (FIG. 6) is substantially similar to the interaction of actuation sled 210 and staple pusher 160 (see FIGS. 22-23) and will not be discussed in detail herein. Further still, distal end 710 is adapted to cooperate with staple pusher 260 (FIG. 26) or staple pusher 360 (FIG. 28). In this embodiment, the lateral and longitudinal offset of the cam wedges are enhanced by providing drive surfaces wherein the first drive angle is less than the second drive angle. This arrangement of drive angles enhances staple pusher stability, thereby minimizing tilting or rotation and further reduces uneven firing of staples 50.

Figure 54:
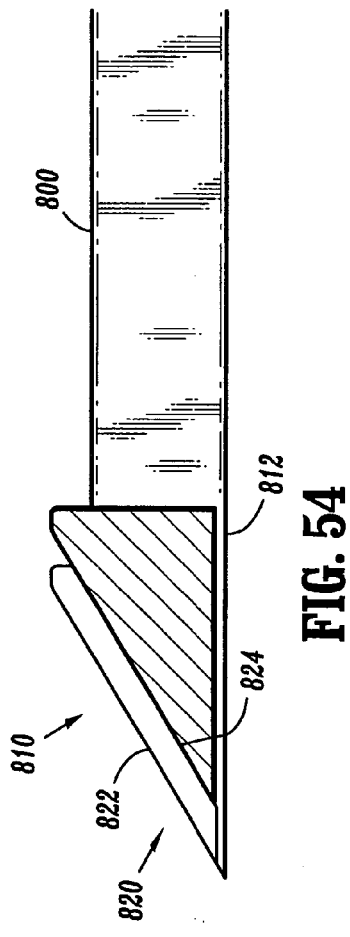
FIG. 54 is a side cross-sectional view of an end portion of an actuation member according to another embodiment of the present disclosure.

FIG. 54 illustrates a portion of an actuation member 800 and includes a distal end 810 having the same or substantially similar components as actuation sled 310 (FIG. 30). Distal end 810 includes a base 812, a first camming member 820, and a second camming member 840 (not shown). First and second camming members 820, 840 include respective first or leading cam wedges 822, 842 and respective second or trailing cam wedges 824, 844. The configuration and relationships between the components of distal end 810 are substantially similar to those components of actuation sled 310 and will not be described in detail herein. Essentially, distal end 810 includes actuation sled 310 using reference characters 8xx in lieu of 3xx used in describing actuation sled 310. In addition, actuation member 800 and distal end 810 may be substituted for actuation sled 310 in staple cartridge 40'. The interaction of distal end 810 and staple pusher 160 (FIG. 6) is substantially similar to the interaction of actuation sled 310 and staple pusher 160 (see FIGS. 35-36) and will not be discussed in detail herein. Further still, distal end 810 is adapted to cooperate with staple pusher 260 (FIG. 26) or staple pusher 360 (FIG. 28). In this embodiment, the lateral and longitudinal offset of the cam wedges improves the stability of the staple pusher during firing.

FIG. 55 illustrates a portion of an actuation member 900 and includes a distal end 910 having the same or substantially similar components as actuation sled 410 (FIG. 37). Distal end 910 includes a base 912, a first camming member 920, and a second camming member 940 (not shown). First and second camming members 920, 940 include respective first or leading cam wedges 922, 942 and respective second or trailing cam wedges 924, 944. The configuration and relationships between the components of distal end 910 are substantially similar to those components of actuation sled 410 and will not be described in detail herein. Essentially, distal end 910 includes actuation sled 410 using reference characters 9xx in lieu of 4xx used in describing actuation sled 410. In addition, actuation member 900 and distal end 910 may be substituted for actuation sled 410 in staple cartridge 40'. The interaction of distal end 910 and staple pusher 460 (FIG. 42A) is substantially similar to the interaction of actuation sled 410 and staple pusher 460 (see FIGS. 43-44) and will not be discussed in detail herein.

FIG. 56 illustrates a portion of an actuation member 1000 and includes a distal end 1010 having the same or substantially similar components as actuation sled 510 (FIG. 45). Distal end 1010 includes a base 1012, a first camming member 1020, and a second camming member 1040 (not shown). First and second camming members 1020, 1040 include respective first or leading cam wedges 1022, 1042 and respective second or trailing cam wedges 1024, 1044. The configuration and relationships between the components of distal end 1010 are substantially similar to those components of actuation sled 510 and will not be described in detail herein. Essentially, distal end 1010 includes actuation sled 510 using reference characters 10xx in lieu of 5xx used in describing actuation sled 510. In addition, actuation member 1000 and distal end 1010 may be substituted for actuation sled 510 in staple cartridge 40'. The interaction of distal end 1010 and staple pusher 160 (FIG. 6) is substantially similar to the interaction of actuation sled 510 and staple pusher 160 (see FIGS. 50-51) and will not be discussed in detail herein. Further still, distal end 1010 is adapted to cooperate with staple pusher 260 (FIG. 26) or staple pusher 360 (FIG. 28).

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure. By way of example only, it is contemplated that the drive angles of various surfaces of the cam wedges may differ between cam wedges of the same actuation mechanism or that the receiving angles of the staple pusher receiving surfaces may differ as between the cam members of the same staple pusher, or both.

What is claimed is:
1. A staple pusher comprising:
a body defining a longitudinal axis, the body including:

a first cam surface configured to facilitate camming motion and being angled at a first oblique angle relative to the longitudinal axis, the first cam surface having a proximal end and a distal end;

a second cam surface configured to facilitate camming motion and being angled at a second oblique angle relative to the longitudinal axis, the second cam surface having a proximal end and a distal end, wherein the second cam surface is longitudinally and laterally offset from the first cam surface; and at least one pusher plate supported by the first and second cam surfaces, the at least one pusher plate having a first end coupled to the body and a second end configured to receive a staple.

2. The staple pusher of claim 1, wherein each cam surface defines a first receiving angle and a second receiving angle.

3. The staple pusher of claim 2, wherein the first receiving angle is greater than the second receiving angle.

4. The staple pusher of claim 3, wherein the first receiving angle is about 35° and the second receiving angle is about 20°.

5. The staple pusher of claim 4, wherein the cam surfaces are substantially parallel to each other.

6. The staple pusher of claim 5, wherein each pusher plate is substantially parallel to the cam surfaces.

7. The staple pusher of claim 1, wherein the first cam surface is longitudinally offset from the second cam surface by about two-thirds of a length of the at least one pusher plate.

8. The staple pusher of claim 1, wherein the first oblique angle is different from the second oblique angle.

9. The staple pusher of claim 1, wherein the first and second cam surfaces define a gap therebetween.

* * * * *